(12) United States Patent
Jabbarzadeh et al.

(10) Patent No.: US 10,786,468 B2
(45) Date of Patent: Sep. 29, 2020

(54) DEACETYLNEMORONE ABIETANE DITERPENOIDS FOR USE IN CANCER TREATMENT

(71) Applicant: University of South Carolina, Columbia, SC (US)

(72) Inventors: Ehsan Jabbarzadeh, Columbia, SC (US); Wesley F. Taylor, Cayce, SC (US); Sara Eslambolchimoghada, Columbia, SC (US)

(73) Assignee: University of South Carolina, Columbia, SC (US)

( * ) Notice: Subject to any disclaimer, the term of this patent is extended or adjusted under 35 U.S.C. 154(b) by 11 days.

(21) Appl. No.: 16/004,550

(22) Filed: Jun. 11, 2018

(65) Prior Publication Data

US 2018/0369165 A1 Dec. 27, 2018

Related U.S. Application Data

(60) Provisional application No. 62/518,051, filed on Jun. 12, 2017, provisional application No. 62/628,415, filed on Feb. 9, 2018.

(51) Int. Cl.
*A61K 31/122* (2006.01)
*A61P 35/02* (2006.01)
*A61K 31/7072* (2006.01)

(52) U.S. Cl.
CPC ............ *A61K 31/122* (2013.01); *A61P 35/02* (2018.01); *A61K 31/7072* (2013.01); *A61K 2300/00* (2013.01)

(58) Field of Classification Search
USPC .......................................................... 514/680
See application file for complete search history.

(56) References Cited

FOREIGN PATENT DOCUMENTS

WO WO 2007/061874 * 5/2007

OTHER PUBLICATIONS

Choudary et. al.(Phytochemistry Letters (2013) 6:139-143). (Year: 2013).*
Burnistova et. al. (Journal of Natural Products (2013) 76:1413-1423). (Year: 2013).*
Basmadjian et al., "Cancer Wars: Natural Products Strike Back", Frontiers in Chemistry, 2, 2014. p. 20.
Burmistrova et al., "Antiproliferative Activity of Abietane Diterpenoids Against Human Tumor Cells", Journal of Natural Products, 76-8, 2013, pp. 1413-1423.
Decicco-Skinner, et al., "Endothelial cell tube formation assay for the in vitro study of angiogenesis." Journal of Visualized Experiments, 2014(91): p. e51312-e51312.
Driver, et al. "The costs of diabetic foot: the economic case for the limb salvage team," Journal of vascular surgery, 2010. 52(3): p. 17S-22S.
Hosseinzadeh et al., "Review of the Pharmacological and Toxicological Effects of *Salvia leriifolia*," Iranian Journal of Basic Medical Sciences, 12-1, 2009, pp. 1-8. (Abstract only).
Hussein et al., "New adduct of abietane-type diterpene from Salvia leriifolia Benth.," Nat Prod Res., 30(13), 2016, pp. 1511-1516. (Abstract only).
Kuhn, et al., "Balancing the pressure ulcer cost and quality equation, " Nursing economic$, 1991, 10(5): p. 353-359.
Merck & Co., "The Merck Index", 14$^{th}$ ed., Whitehouse Station, NJ, 2006.
Newman et al., "Natural Products as Sources of New Drugs Over the Last 25 Years", Journal of Natural Products, 70-3, 2007, pp. 461-477.
Sen, et al., "Human skin wounds: a major and snowballing threat to public health and the economy," Wound Repair and Regeneration, 2009. 17(6): p. 763-771.
Siegel et al., "Cancer Statistics 2016", CA: A Cancer Journal for Physicians, 66-1, 2016, pp. 7-30.
Singer, et al., "Cutaneous wound healing," New England journal of medicine, 1999. 341(10): p. 738-746.
Tecilazich, et al., "Emerging drugs for the treatment of diabetic ulcers," Expert opinion on emerging drugs, 2013. 18(2): p. 207-217.
Wang, et al., "Enhanced keratinocyte proliferation and migration in co-culture with fibroblasts," PloS one, 2012. 7(7): p. e40951.

(Continued)

*Primary Examiner* — Marcos L Sznaidman
(74) *Attorney, Agent, or Firm* — Dority & Manning, P.A.

(57) ABSTRACT

A deacetylnemorone abietane diterpenoid is utilized in the prevention of growth and development of pathogenic cells, e.g., cancer cells. The deacetylnemorone can have the following structure:

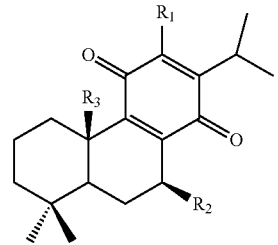

or a tautomer there of in which $R_1$, $R_2$, and $R_3$ are independently selected from —H, $C_{1-10}$ alkyl, $C_{1-10}$ alkoxy, $C_{1-10}$ alkenyl, $C_{1-10}$ alkenoxy, —OH, —OAc, —CHO, -Ph, —$OC_6H_5$, —$OC_6H_4OH$, —$COC_6H_5$, —$OCONH_2$, —$OCONHCH_3$, —$OCOC_6H_4NH_2$, —$NH_2$, or =O.
The deacetylnemorone shows efficacy in treatment and prevention of a wide range of cancer types as well as other neoplastic diseases as a chemo-preventative, a primary or secondary cytotoxic agent, a sensitizer for other therapies, or one component of a combinatorial treatment.

14 Claims, 18 Drawing Sheets

(56) References Cited

OTHER PUBLICATIONS

Wang et al., "Anti-Proliferative Effect of Jesridonin on Paclitaxel-Resistant EC109 Human Esophageal Carcinoma Cells", International Journal of Molecular Medicine, 2017, pp. 645-653.
Zhang et al., "Oridonin Effectively Reverses the Drug Resistance of Cisplatin Involving Induction of Cell Apoptosis and Inhibition of MMP Expression in Human Acute Myeloid Leukemia Cells", Saudi Journal of Biological Sciences, 24-3, 2017, pp. 678-686.
Related U.S. Patent Applications, Jul. 25, 2018.
U.S. Appl. No. 16/004,529, filed Jun. 11, 2018, Jabbarzadeh, et al., Abietane Diterpenoid 7-Acetoxyroyleanones for Use in Cancer Treatment.
U.S. Appl. No. 16/004,538, filed Jun. 11, 2018, Jabbarzadeh, et al., Pimarane Diterpenoids for Use in Cancer Treatment.
U.S. Appl. No. 16/004,576, filed Jun. 11, 2018, Jabbarzadeh, et al., Pimarane Diterpenoids for Use in Wound Healing and Angiogenesis.

\* cited by examiner

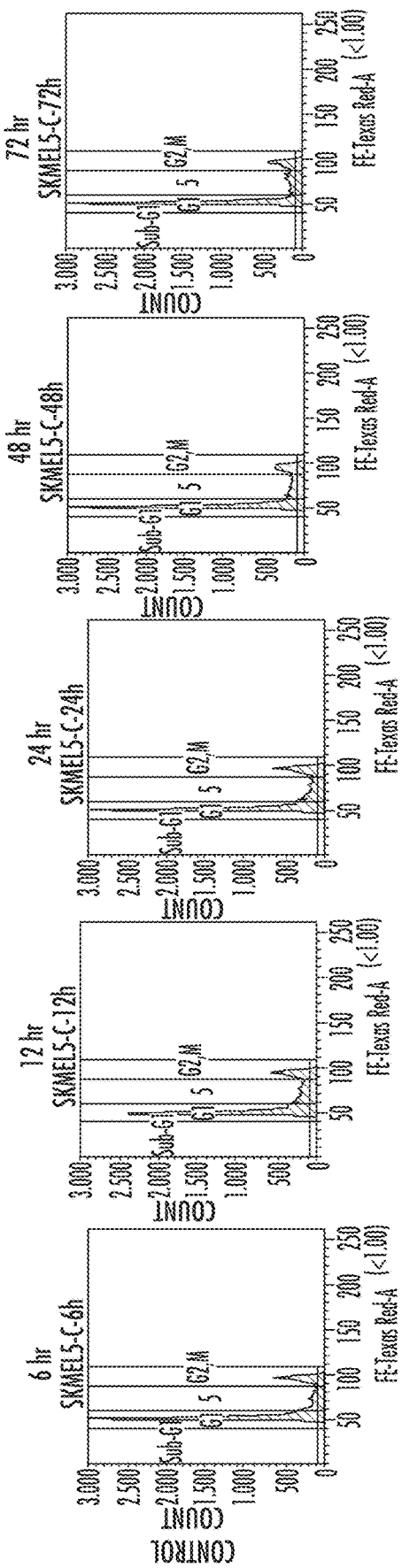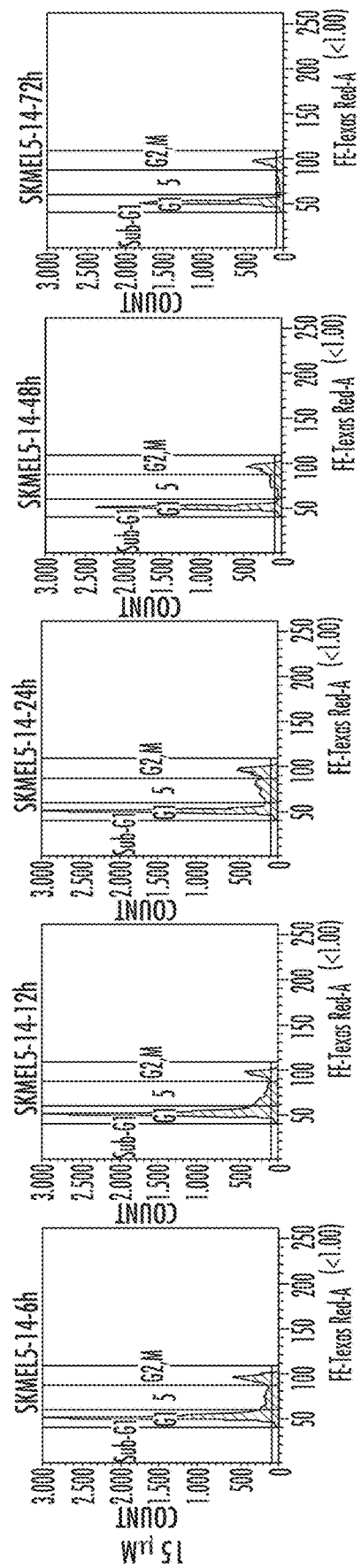
FIG. 18

DEACETYLNEMORONE ABIETANE DITERPENOIDS FOR USE IN CANCER TREATMENT

CROSS REFERENCE TO RELATED APPLICATION

This application claims filing benefit of U.S. Provisional Patent Application Ser. No. 62/518,051 entitled "Use of a Newly Discovered Sesterterpenoid for Cancer Treatment" having a filing date of Jun. 12, 2017, and U.S. Provisional Patent Application Ser. No. 62/628,416 entitled "Deacetylnemorone Abietane Diterpenoids for Use in Cancer Treatment" having a filing date of Feb. 9, 2018, both of which are incorporated herein by reference for all purposes.

FEDERAL RESEARCH STATEMENT

This invention was made with Government support under Grant No. 1631439, awarded by the National Science Foundation. The Government has certain rights in the invention.

BACKGROUND

Cancers remain the cause of poor health and early death throughout the world. Despite advances in treatment, cancer remains the second leading cause of death in the United States and is the leading cause of death in 21 states as of 2016. Further, the probability of being diagnosed with an invasive cancer was found to be 42% for men and 37.6% for women living in the United States according to a study by Siegel and others ("Cancer statistics, 2016," *CA Cancer J Clin*, vol. 66, no. 1, pp. 7-30, 2016 January-February 2016). The same study reported that 582,623 deaths in 2012 were a result of cancer and projected that 1,685,210 new cancer cases and 595,690 cancer deaths would occur during 2016.

Treatment of cancers has traditionally been accomplished through one of, or a combination of, chemotherapy, surgery, radiotherapy, immunotherapy, and hormone therapy, among others. Unfortunately, differences in genetic expression, drug sensitivity, cell morphology, and metastatic targets across the dozens of known cancer types has stymied the long-term success of treatments. Acquired drug resistance in response to chemotherapy remains another hurdle in cancer treatment that demands a diverse arsenal of cytotoxic agents. Cancer recurrence and distant metastases, potentially explained by inherently robust and drug resistant cancer stem cells, further hinder positive prognoses in cancer patients. It is hypothesized that cancer stem cells can remain dormant and undetected in the body for years before reactivating and beginning the formation of a new tumor. As such, cancer recurrence and distant metastases continue to plague cancer patients after months or even years of remission using current treatments.

The role of immune cells in combating aggressive tumors has become increasingly recognized in the medical community and has led to new approaches for cancer therapies. FDA approval of the first therapeutic cancer vaccine, sipuleucel-T, and other cancer immunotherapy drugs, including monoclonal antibodies such as ipilimumab, in addition to increased understanding of the immune system's role in the tumor microenvironment, has led to a call for small molecules capable of regulating immune activity and supporting tumor death.

In spite of such advances, many shortcomings and disadvantages of current chemotherapeutics and other cancer treatments are readily apparent. The hair loss, nausea, vomiting, loss of appetite, compromised immune system, and other side effects commonly associated with a cancer therapy are often a consequence of the currently utilized treatments and not the disease itself.

Unfortunately, a push to develop chemotherapeutic drugs capable of targeting a specific molecule or cancer-associated signaling pathway with reduction in side effects has failed to yield the expected improvements in patient prognoses. This is largely due to the ability of cancer cells to utilize a combination of many different cellular mechanisms to enhance viability. In many cases, cancer cells are able to circumvent apoptosis induced from targeted therapies by simply activating other survival pathways after the initial treatment.

Natural products are a historically successful source of medicinally active compounds with fewer unwanted side effects, especially in regard to chemotherapeutics. In fact, 63% of cancer drugs used between 1981 and 2006 were natural products, were inspired by natural products, or were synthesized from a natural pharmacophore. Medicinally active compounds derived from natural materials have the potential to provide targeted cytotoxic and immune modulating responses while limiting the taxing side effects associated with currently utilized cancer treatments. The use of natural products attempts to balance a robust ability to target numerous pathways simultaneously with a historical record of safe human consumption and benign side effects.

There is a need to discover and optimize the use of novel cytotoxic compounds with low $IC_{50}$ values, diverse biological targets, immune regulatory capability, and diminished side effects. In addition, there is a need for new treatments engineered to target pathogenic cells both during initial treatment of cancers and after remission has occurred in order to prevent cancer recurrence. New treatments based upon natural materials that can provide efficacy with benign or limited side effects would be of great benefit.

SUMMARY

According to one embodiment, disclosed is a method for inhibiting the growth and development of cancer cells. The method includes delivering a deacetylnemorone abietane diterpenoid to an area comprising cancer cells. Beneficially, the method shows efficacy for a large variety of different cancer cell types.

Also disclosed is a method for preventing angiogenesis, for instance in the treatment of cancer. The method includes delivering a deacetylnemorone abietane diterpenoid to an area comprising endothelial cells.

Also disclosed is a composition configured for inhibiting the growth and development of cancer cells and/or inhibiting angiogenesis that includes a deacetylnemorone abietane diterpenoid and a pharmaceutically acceptable carrier. The deacetylnemorone can have the following structure:

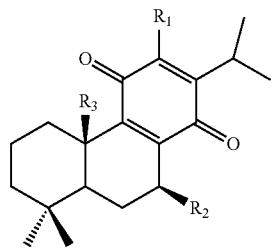

or a tautomer there of in which $R_1$, $R_2$, and $R_3$ are independently selected from —H, $C_{1-10}$ alkyl, $C_{1-10}$ alkoxy, $C_{1-10}$ alkenyl, $C_{1-10}$ alkenoxy, —OH, —OAc, —CHO, -Ph, —$OC_6H_5$, —$OC_6H_4OH$, —$COC_6H_5$, —$OCONH_2$, —$OCONHCH_3$, —$OCOC_6H_4NH_2$, —$NH_2$, or =O.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 18 presents a histogram of PI expression as measured by flow cytometry for SKMEL5 cells treated with control or 15 µM of a deacetylnemorone.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is generally directed to the utilization of an abietane diterpenoid that has been found to exhibit efficacy against a large variety of cancer cells and that has also been found to prevent angiogenesis. More specifically, disclosed are methods for inhibiting the growth and development of pathogenic cells, and in one particular embodiment of cancer cells, by use of a deacetylnemorone abietane diterpenoid. The deacetylnemorone abietane diterpenoids encompassed herein can generally have a structure as follows:

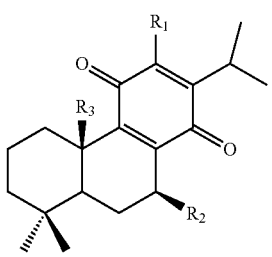

or a tautomer there of in which $R_1$, $R_2$, and $R_3$ are independently selected from —H, $C_{1-10}$ alkyl, $C_{1-10}$ alkoxy, $C_{1-10}$ alkenyl, $C_{1-10}$ alkenoxy, —OH, —OAc, —CHO, -Ph, —$OC_6H_5$, —$OC_6H_4OH$, —$COC_6H_5$, —$OCONH_2$, —$OCONHCH_3$, —$OCOC_6H_4NH_2$, —$NH_2$, or =O. In one embodiment, a deacetylnemorone abietane diterpenoid can have a structure as illustrated in FIG. 1.

Figure 1:
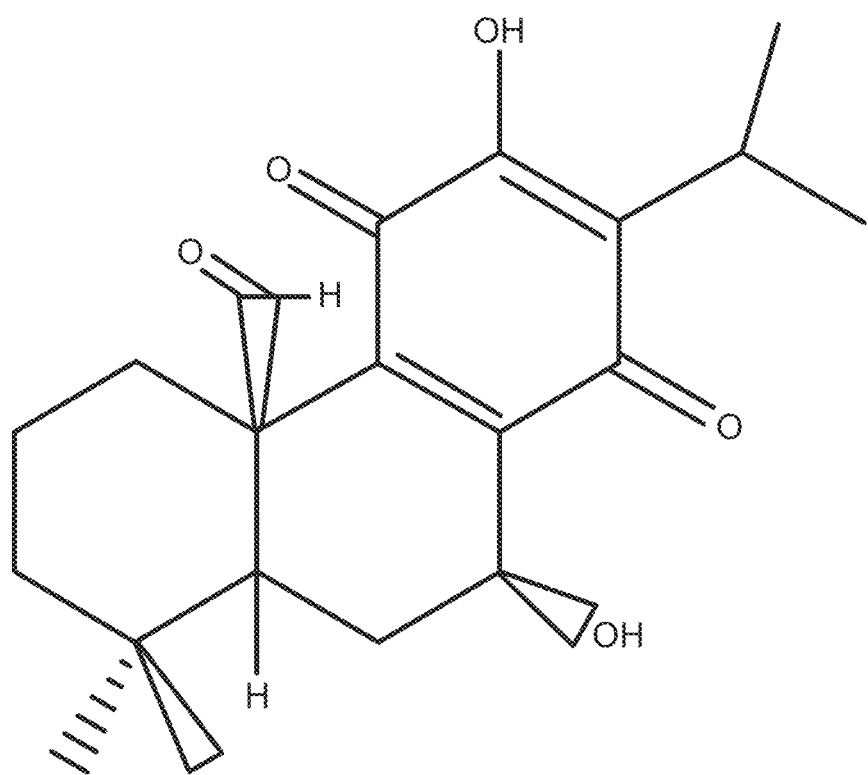
FIG. 1 illustrates the structure of one embodiment of a deacetylnemorone abietane diterpenoid encompassed herein.

The deacetylnemorone of FIG. 1 is an abietane diterpenoid that has been isolated from the plant *Salvia leriifolia*. *Salvia* leriifolia Benth. (vernacular names include Nuruozak and Jobleh) is a perennial herbaceous plant that grows exclusively in south and tropical regions of certain areas of Iran. Unlike other species of the *Salvia* genus, the chemical constituents of *S. leriifolia* are not well recognized. The stem oil of the plant is known to include monoterpenes and sesquiterpenes, and in leaf and flower oils monoterpenes predominate over sesquiterpenes. In recent years, properties of this plant such as the attenuation of morphine dependence, hypoglycemic, antinociceptive and antiinflammatory, antioxidant, anti-ischemia, anticonvulsant, antiulcer effects, antibacterial activities and antimutagenic effects have been evaluated (see, e.g., Hosseinzadeh, et al. Iranian Journal of Basic Medical Sciences, 12:1, 2009, 1-8). However, the abietane diterpenoid of FIG. 1 has not been previously isolated from the plant and the efficacy of this compound isolated from the *S. leriifolia* as well as derivatives as described herein in inhibition of pathogenic cells as well as in inhibition of angiogenesis has not been previously recognized.

Deacetylnemorone as illustrated in FIG. 1 was isolated from *S. leriifolia* and purified before being exposed, in vitro, to immortalized tumor cells. Deacetylnemorone of *S. leriifolia* as well as derivatives and tautomers as encompassed herein can display efficacy against a broad spectrum of pathogenic cells involved in multiple different types of cancers and other neoplastic disorders. Beneficially, the described deacetylnemorones can show efficacy as a chemopreventative, a primary cytotoxic agent, a sensitizer for other therapies, one component of a combinatorial anti-cancer treatment, or an anti-angiogenic agent.

As an effective inhibitor of angiogenesis, deacetylnemorone abietane diterpenoids as described can be a suitable therapeutic alternative for treatment of disorders in which excessive blood vessel growth contributes to the pathology, including cancer, rheumatoid arthritis, and psoriasis. For example, a deacetylnemorone may be suited for treatment of atherosclerosis due to its anti-angiogenic properties. Inhibiting angiogenesis may prevent intraplaque angiogenesis, thereby limiting plaque growth, destabilization, and subsequent rupture.

Deacetylnemorone abietane diterpenoids as encompassed herein can exhibit anti-proliferative or cytotoxic effects in vitro after about 48 hours of exposure (e.g., about 48 hr. to about 72 hr. of exposure) and have shown efficacy against a number of immortalized cancer cell lines. For example, disclosed materials and methods can be utilized to inhibit growth and development of cancer cells including, but without limitation to, osteosarcoma cells, ovarian adenocarcinoma cells, breast adenocarcinoma cells, colorectal carcinoma cells, as well as pathogenic cells present in angiogenic disorders. Beneficially, the deacetylnemorones can exhibit efficacy against cancer cells exhibiting resistance to other, more traditional chemotherapies such as FdUrd utilized in treatment of colorectal cancer and doxorubicin utilized in treatment of a wide variety of cancers. For example, deacetylnemorone abietane diterpenoids as described can inhibit growth and/or development of pathogenic cells including, without limitation, breast cancer cells, bladder cancer cells, Kaposi's sarcoma cells, lymphoma cells, ovarian cancer cells, prostate cancer cells, central nervous system (CNS) cancer cells, renal cancer cells, melanoma cells, colon cancer cells, non-small cell lung cancer cells, and leukemia cells. The disclosed methods and materials can be particularly beneficial against cells that are untreatable through current methods or that have developed a resistance to other, more traditional treatments.

The materials and methods can be targeted in one embodiment against cancer stem cells, which can aid in prevention of cancer metastasis and recurrence.

In one embodiment, disclosed materials can be utilized to target cancer tumors, and can do so without affecting healthy cells, leading to development of treatment protocols having fewer side effects.

As described further in the Examples section below, in vitro toxicity screening has demonstrated a synergistic relationship between the disclosed materials and the commonly used chemotherapy drug FdUrd in inducing cell death in colorectal carcinoma cells. As such, disclosed materials can be utilized in one particular embodiment in combination with more traditional chemotherapy and in particular with more traditional colorectal chemotherapy such as FdUrd. Further, disclosed materials can act synergistically with other treatments in clinical use or clinical trials including, but not limited to, surgical resection of tumors, radiation therapy, hormone therapy, immunotherapy, cancer vaccines, etc.

The clinical application and dosage of disclosed materials can be tailored to the particular cancer cell of interest as well as to tumor size and stage, patient size, patient medical history, method of delivery, etc., according to methods as are generally known in the art. Use of these compounds in combination with any number of other bioactive agents, e.g., chemotherapy agents such as FdUrd, has the potential to elicit desirable responses in a large variety of cancer cell types.

By way of example and without limitation, one or more deacetylnemorones as described herein can be utilized in combination with other bioactive agents including classes of antineoplastic drugs including alkaloids/natural products, alkylating agents, antibiotics, antimetabolites, enzymes, farnesyl transferase inhibitors, immunomodulators, immunotoxins, monoclonal antibodies, oligonucleotides, platinum complexes, retinoids, tyrosine kinase inhibitors, androgens, antiadrenals, antiandrogens, antiestrogens, antiprogestins, aromatase inhibitors, estrogens, LH-RH analogs, progestogens, and somatostatin analogs. Examples of common chemotherapeutics on the market that can be utilized in conjunction with deacetylnemorone can include, without limitation, the alkaloids paclitaxel, vinblastine, and vincristine; the antimetabolites gemcitabine, 5-fluoruracil, and methotrexate; the antibiotic or antibiotic derivatives doxorubicin, daunorubicin, and bleomycin; the hormonal antineoplastics tamoxifen, diethylstilbestrol, and polyestradiol phosphate; and the immonomodulators sipuleucel-T, interferon-5, and nivolumab.

When utilized in conjunction with another therapy, disclosed materials can be administered at the same time as the other therapy, e.g., together in a single composition, or at a different time or on a different schedule, e.g., prior to and/or following administration of a second bioactive agent.

The methods can be utilized in vivo for treatment of cancer or in vitro for study of pathogenic cells or tissue. In order for disclosed materials to be effectively utilized in a clinical therapy, a deacetylnemorone can be delivered so as to be provided with suitable bioavailability. According to one treatment method, a composition including a deacetylnemorone and a pharmaceutically compatible carrier can be delivered to targeted cells via any pharmaceutically acceptable delivery system. In general, a deacetylnemorone may be administered to a subject according to known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Osmotic mini-pumps may also be used to provide controlled delivery of a deacetylnemorone through cannulae to the site of interest, such as directly into a metastatic growth. In certain embodiments, a deacetylnemorone can be administered directly to the area of a tumor or cancer tissue, including administration directly to the tumor stroma during invasive procedures. A deacetylnemorone may also be placed on a solid support such as a sponge or gauze for administration.

Pharmaceutically acceptable carriers include, but are not limited to, saline, buffered saline, glucose in saline, etc. Solid supports, liposomes, nanoparticles, microparticles, nanospheres or microspheres may also be used as carriers for administration of deacetylnemorone. As used herein the term "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The appropriate dosage ("therapeutically effective amount") of the deacetylnemorone can depend, for example, on the severity and course of the cancer, whether the deacetylnemorone is administered for therapeutic purposes or in prevention of side effects of a chemotherapy, previous therapy, the patient's clinical history and response to the deacetylnemorone, and the discretion of the attending physician, among other factors. A deacetylnemorone can be administered to a subject at one time or over a series of treatments and may be administered to the subject at any time.

In one embodiment, a therapeutically effective amount of a deacetylnemorone can be in the range of about 0.001 mg/kg body weight/day to about 100 mg/kg body weight/day whether by one or more administrations for instance at a concentration of from about 1 mg/mL to about 50 mg/mL. For example, a deacetylnemorone can be administered in an amount of from about 1 mg/kg body weight per day to about 50 mg/kg body weight/day, in some embodiments. For instance, the deacetylnemorone can be provided to the targeted site, e.g., a tumor or an in vitro deposit of cancer cells, such that the deacetylnemorone is at a concentration of about 10 millimolar (10 mM) or greater at the site of contact, for instance at a concentration of from about 10 mM to about 50 mM in some embodiments. As expected, the dosage can be dependent on the condition, size, age and condition of the patient.

A deacetylnemorone may be administered, as appropriate or indicated, in a single dose as a bolus or by continuous infusion, or as multiple doses by bolus or by continuous infusion. Multiple doses may be administered, for example, multiple times per day, once daily, multiple times per week, every 2, 3, 4, 5, 6 or 7 days, weekly, every 2, 3, 4, 5 or 6 weeks or monthly. However, other dosage regimens may be useful. The progress of this therapy is easily monitored by conventional techniques.

It can be advantageous to formulate oral or parenteral compositions in dosage unit form for ease of administration and uniformity of dosage. Dosage unit form as used herein includes physically discrete units suited as unitary dosages for the subject to be treated; each unit may contain a predetermined quantity of active compound calculated to produce the desired therapeutic effect in association with the required pharmaceutical carrier. The specification for the dosage unit forms of the application is dictated by and directly dependent on the unique characteristics of the active compound and the particular therapeutic effect to be achieved, and the limitations inherent in the art of compounding such an active compound for the treatment of individuals.

Pharmaceutical compositions for parenteral, intradermal, or subcutaneous injection can include pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. A composition can contain minor amounts of auxiliary substances such as wetting or emulsifying agents, pH buffering agents and the like that can enhance the effectiveness of the active ingredient. Proper fluidity may be maintained, for example, by the use of coating materials such as lecithin, by the maintenance of the required particle size in the case of dispersions and by the use of surfactants. A composition may also contain adjuvants such as preservatives, wetting agents, emulsifying agents and dispersing agents. It may also be desirable to include isotonic agents such as sugars, sodium chloride and the like.

For intravenous administration, suitable carriers include, without limitation, physiological saline, bacteriostatic water, Cremophor EL™ (BASF, Parsippany, N.J.) or phosphate buffered saline (PBS). In all cases, an injectable composition should be sterile and should be fluid to the extent that easy syringability exists. It must be stable under the conditions of manufacture and storage and must be preserved against the contaminating action of microorganisms such as bacteria and fungi. Prevention of the action of microorganisms may be ensured by the inclusion of various antibacterial and antifungal agents such as paraben, chlorobutanol, phenol, sorbic acid and the like. Prolonged absorption of the injectable compositions can be brought about by including in the composition an agent that delays absorption, for example, aluminum monostearate or gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of an orally ingestible composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

When administered orally in liquid form, a liquid carrier such as water, petroleum, oils of animal or plant origin such as peanut oil, mineral oil, soybean oil, or sesame oil, or synthetic oils may be added. A liquid form may further contain physiological saline solution, dextrose or other saccharide solution, or glycols such as ethylene glycol, propylene glycol or polyethylene glycol. When administered in liquid form, a composition can contain from about 0.5 to 90% by weight deacetylnemorone, in one embodiment from about 1 to 50% by weight deacetylnemorone.

For administration by inhalation, the deacetylnemorone can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, a pharmaceutical composition can be formulated for sustained or controlled release of deacetylnemorone. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art.

It is to be understood that the in vivo methods have application for both human and veterinary use. The methods of the present invention contemplate single as well as multiple administrations, given either simultaneously or over an extended period of time.

The present disclosure may be better understood with reference to the Example set forth below.

Example 1

Figure 2:
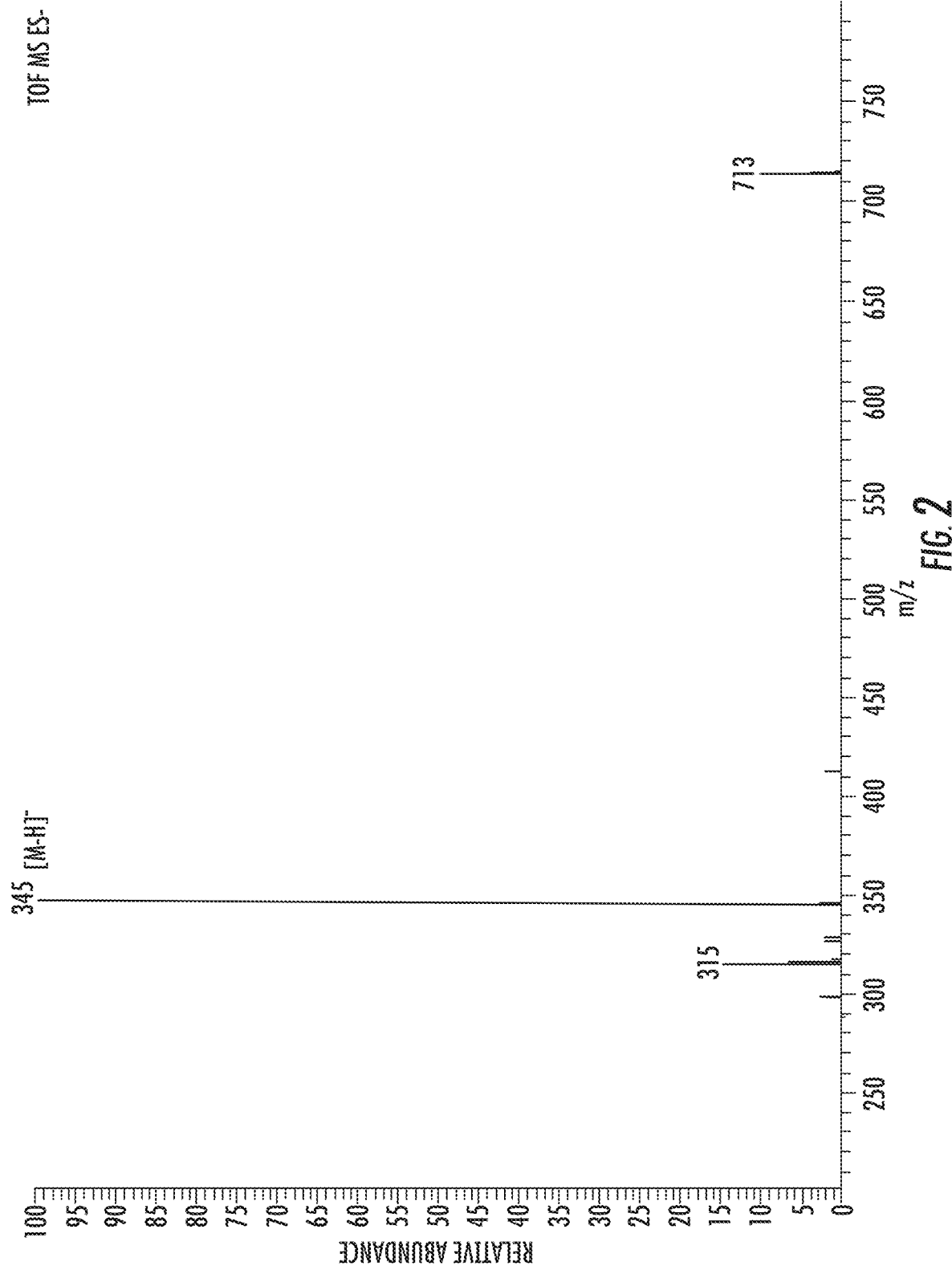
FIG. 2 illustrates the Time of Flight mass spectometry (TOF-MS) spectrum (negative ion mode) of the deacetylnemorone of FIG. 1.
Figure 4:
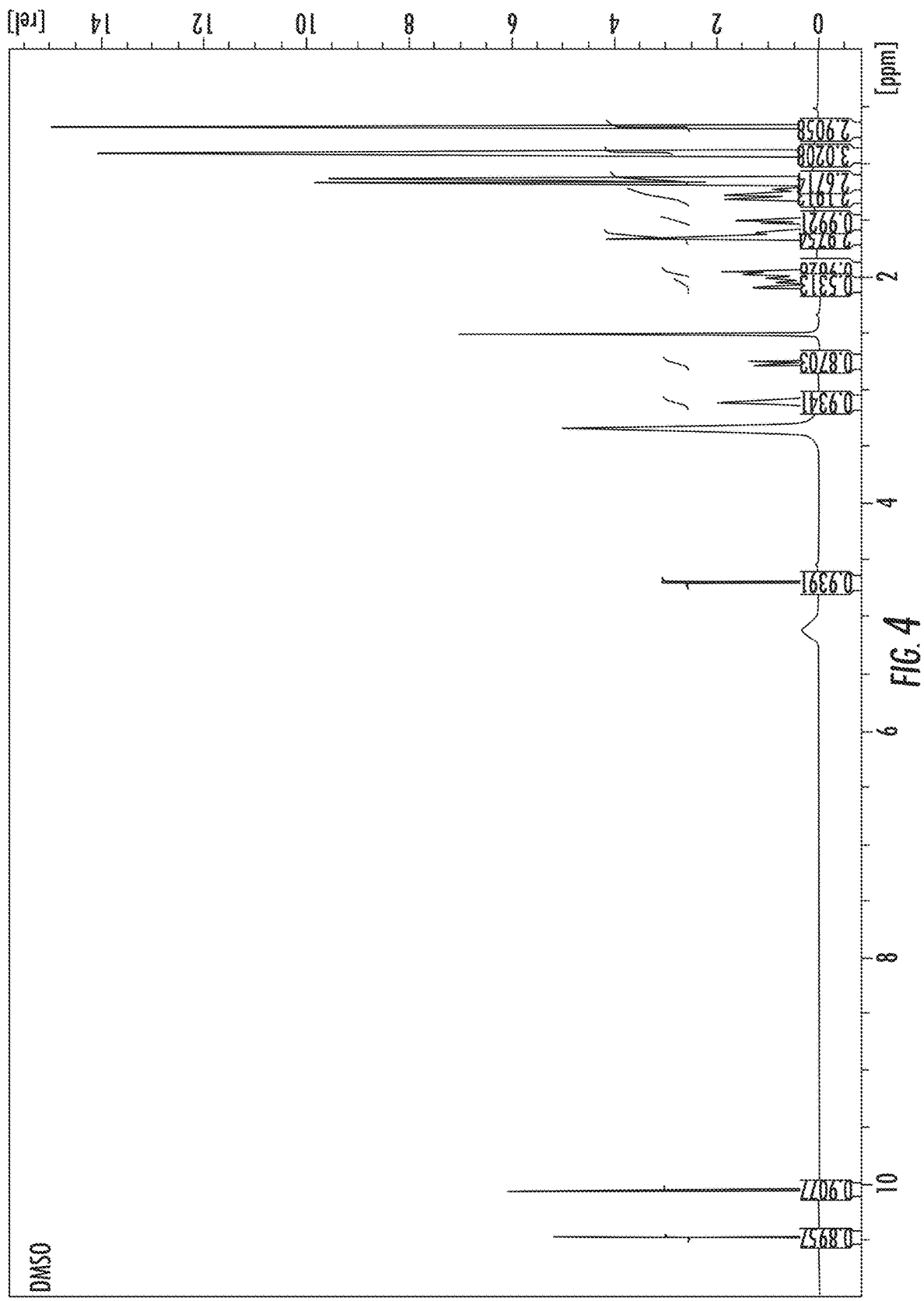
FIG. 4 illustrates the hydrogen nuclear magnetic resonance ($^1$H-NMR) spectrum of the deacetylnemorone of FIG. 1.
Figure 5:
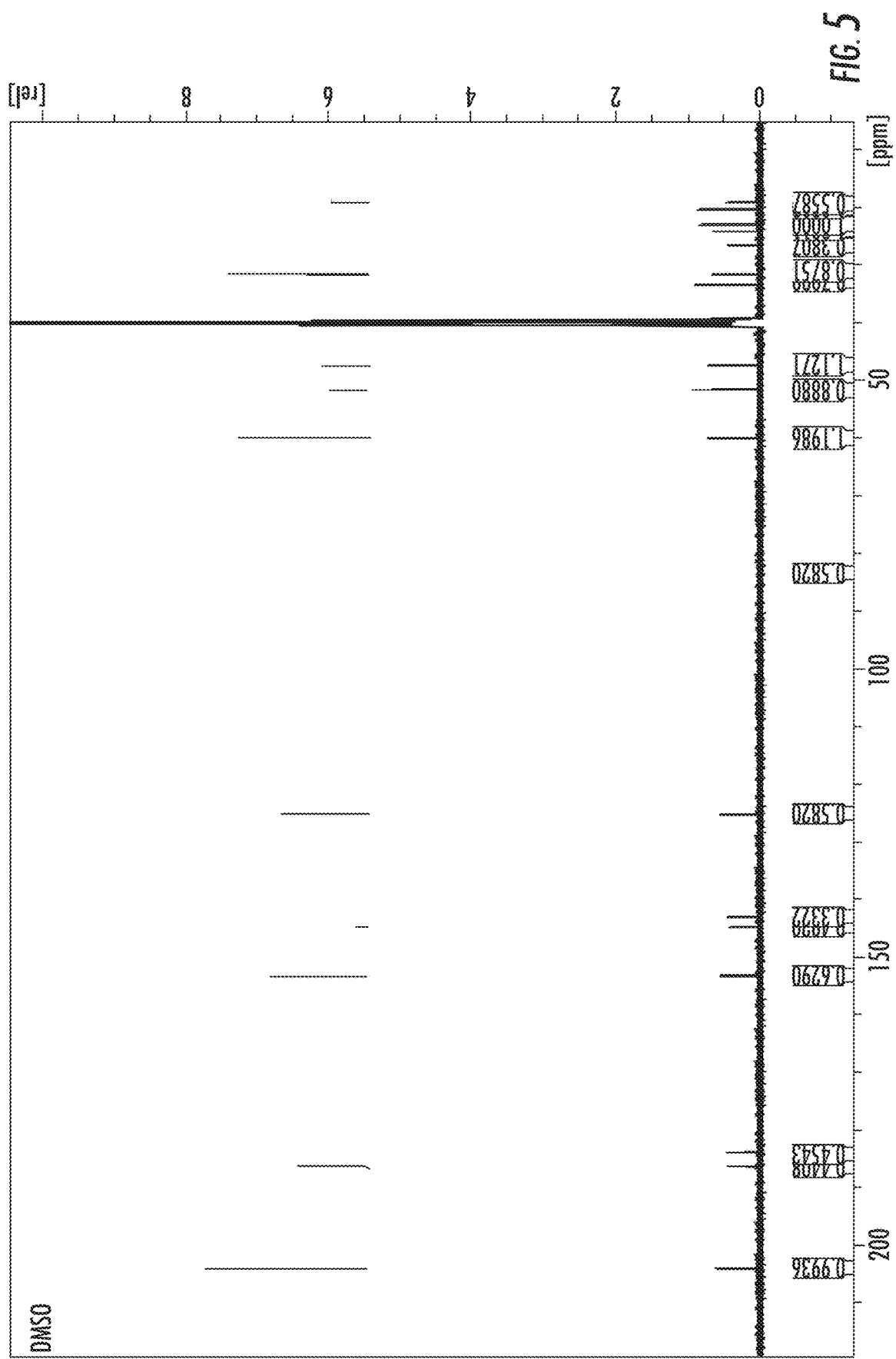
FIG. 5 illustrates the carbon 13 nuclear magnetic resonance ($^{13}$C-NMR) spectrum of the deacetylnemorone of FIG. 1.
Figure 6:
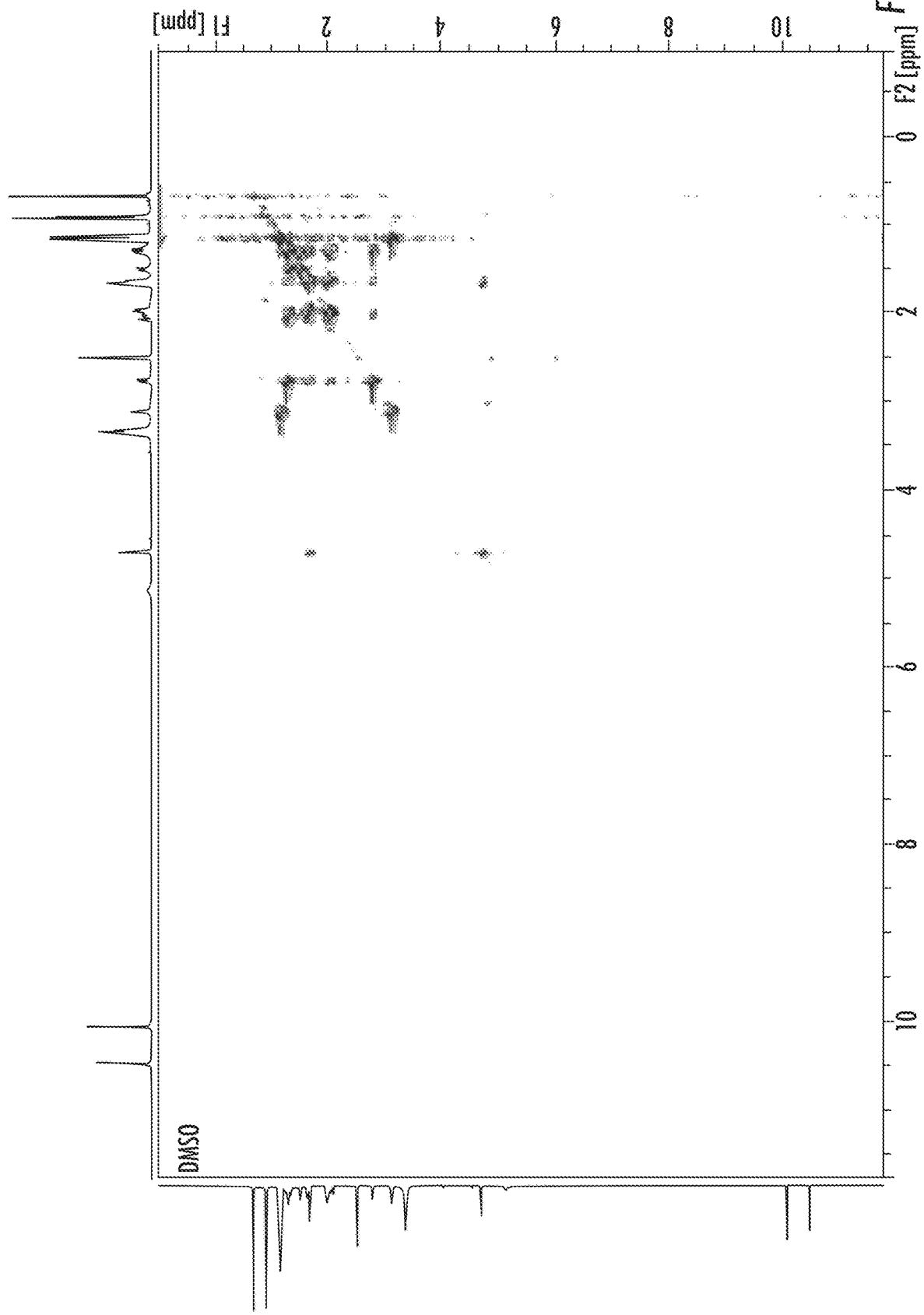
FIG. 6 illustrates the hydrogen correlated spectroscopy (H—H COSY) spectrum of the deacetylnemorone of FIG. 1.
Figure 7:
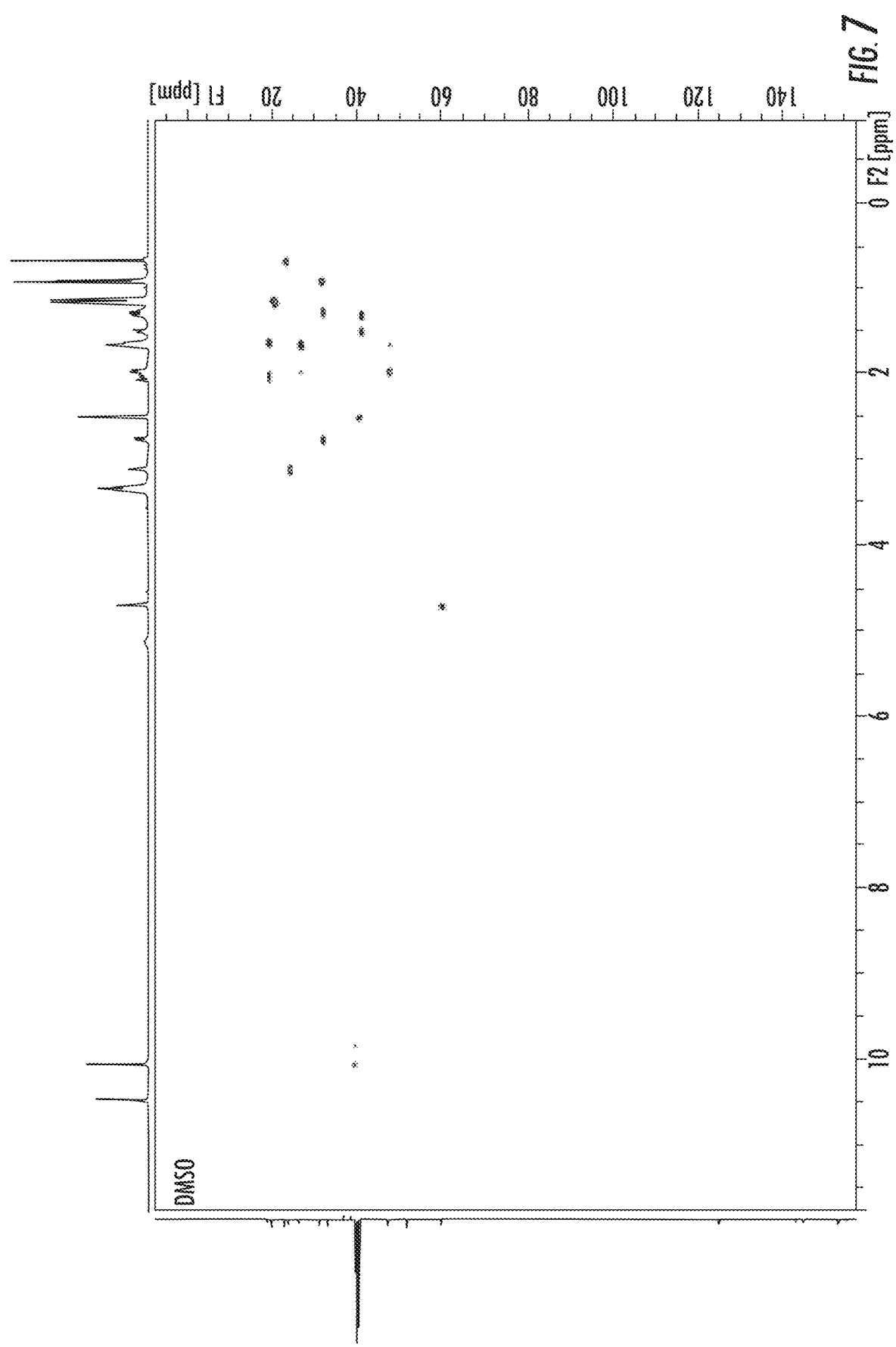
FIG. 7 illustrates the heteronuclear single quantum coherence (HSQC) spectrum of the deacetylnemorone of FIG. 1.
Figure 8:
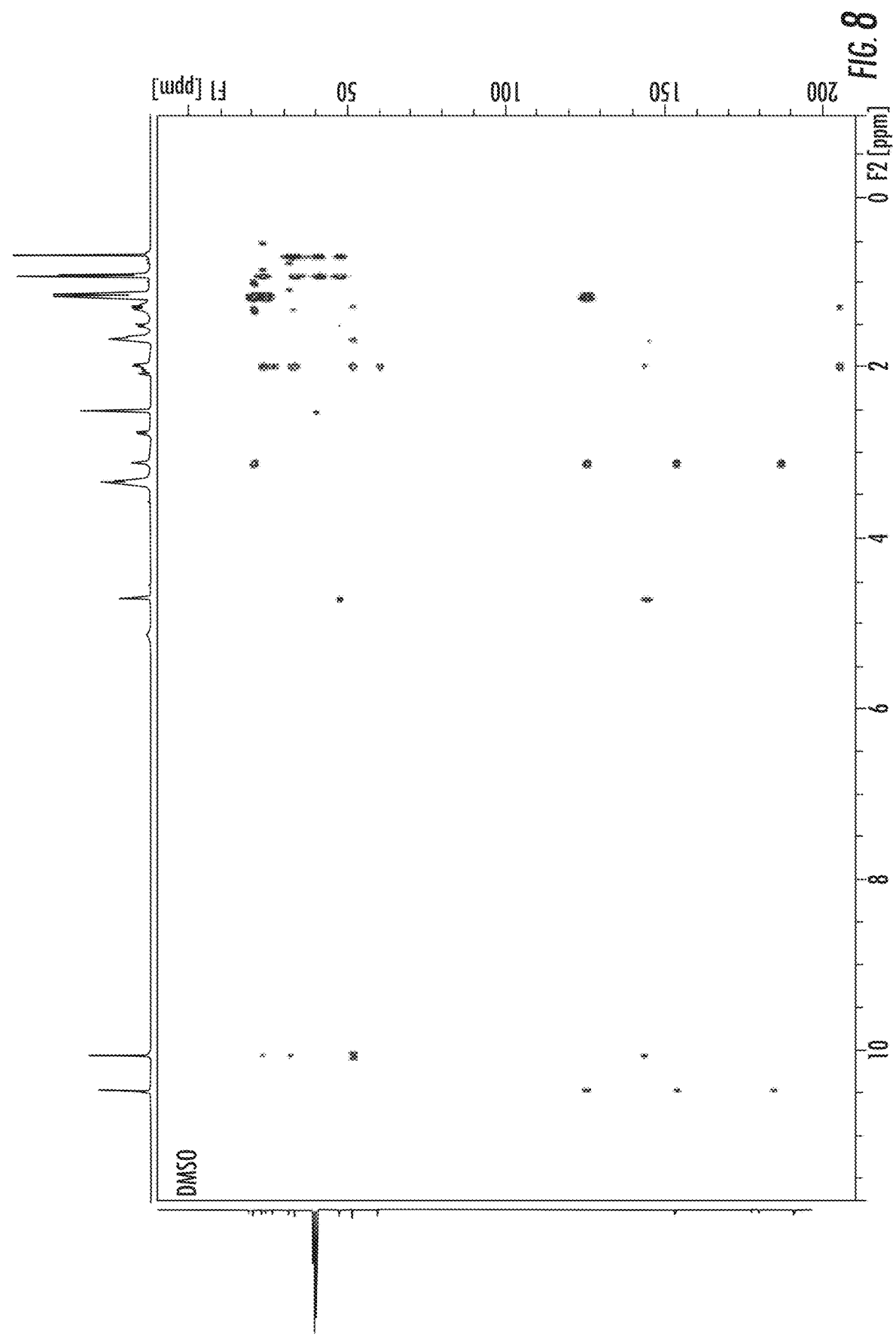
FIG. 8 illustrates the heteronuclear multiple bond correlation (HMBC) spectrum of the deacetylnemorone of FIG. 1 (in DMSO-d6).

The structure of a natural isolated deacetylnemorone (FIG. 1) was established by means of 1D- and 2D-Nuclear Magnetic Resonance (NMR) (COSY (results shown in FIG. 6), HSQC (FIG. 7), and HMBC (FIG. 8)) and the molecular formula was determined by High Resolution Mass Spectrometry (HR-MS) (FIG. 3) and low resolution Time of Flight Mass Spectrometry (TOF-MS) (FIG. 2). NMR spectra (FIG. 4 and FIG. 5) were obtained in DMSO-d6.

Figure 3:
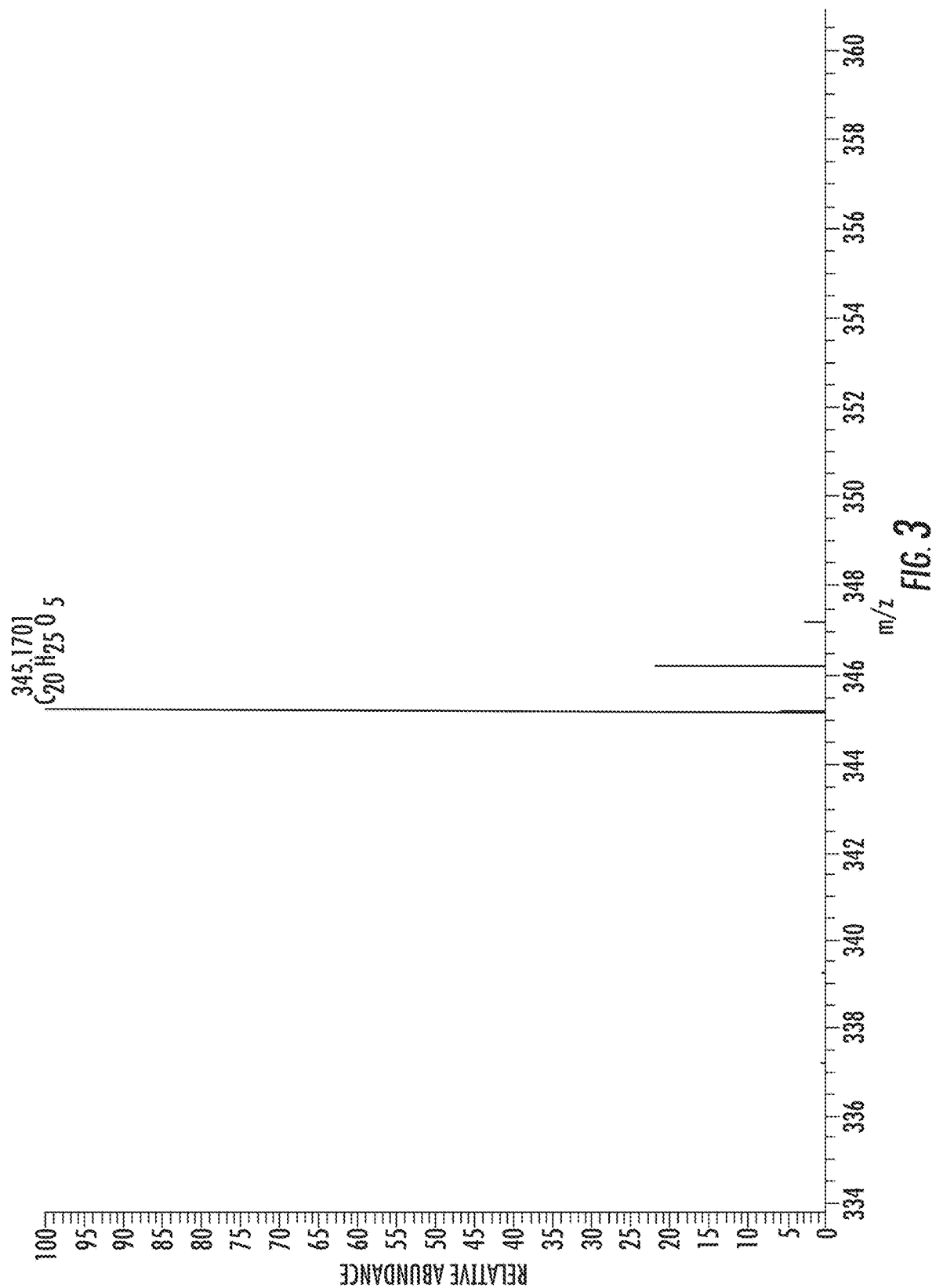
FIG. 3 illustrates the high resolution mass spectometry (HR-MS) spectrum (negative mode) of the deacetylnemorone of FIG. 1.

The deacetylnemorone was found to have a molecular formula as shown in FIG. 1 of $C_{20}H_{26}O_5$ (evidenced by HR-MS ([M-H]$^-$ ion at m/z 345.1707; FIG. 3)). The NMR spectra (FIG. 4, FIG. 5) confirmed molecular formula of $C_{22}H_{30}O5$. Resonance for two tertiary methyls ($\delta$H 0.67 (s, H3-18) and 0.90 (s, H3-19)), two secondary methyls ($\delta$H 1.17 (d, H3-16) and 1.13 (d, H3-17)), and one oxygenated methine ($\delta$H 4.70 9 (t, H-7)) were observed in $^1$H NMR spectrum. Complementary assignment was obtained through analysis of 2D spectra. The NMR spectra confirmed the abietane diterpenoid structure.

Example 2

Materials and Methods
Cell Culture

The human cell lines used for MTS assay screening included MG-63 (osteosarcoma), SK-OV-3 (ovarian adenocarcinoma), MDA-MB-231 (breast adenocarcinoma derived from a metastatic site), HCT 116 (colorectal carcinoma), HCT 116/200 (an FdUrd resistant subclone of HCT 116 cells), A2780ADR (a doxorubicin resistant subclone of the ovarian carcinoma A2780), and HUVEC (normal human umbilical vein endothelial cells). All cells were stored in liquid nitrogen until use. MG-63, SK-OV-3, MDA-MB-231, and HCT 116 cell lines were all obtained from ATCC. A2780ADR cells were obtained from Sigma-Aldrich. HCT 116/200 cells were obtained from Dr. Franklin G. Berger from the Center for Colon Cancer Research. HUVEC cells were obtained from Lonza. MG-63 cells were maintained in MEM medium (Corning) supplemented with 10% Fetal Bovine Essence (VWR) and 1% penicillin/streptomycin solution (Corning). SK-OV-3 cells were maintained in McCoy's 5A Medium (Sigma) supplemented with Fetal Bovine Essence and 1% penicillin/streptomycin. A2780ADR cells were maintained in RPMI 1640 medium (Corning) supplemented with 10% Fetal Bovine Essence and 2 mM L-glutamine (ThermoFisher). MDA-MB-231, HCT 116, and HCT 116/200 cells were all maintained in RPMI 1640 medium supplemented with 10% Fetal Bovine Essence and 1% penicillin/streptomycin. HUVEC cells were maintained in EGM-2 medium (Lonza BulletKit). Cells were incubated at 37° C. and 5% $CO_2$ throughout the experiment.

MTS Assay

Cells were first grown to approximately 80% confluency within 25 cm$^3$ tissue culture flasks (VWR). The cells were washed once with PBS (Corning) before being trypsinized using a 0.25% trypsin, 2.21 mM EDTA, and sodium bicarbonate solution (Corning). Trypsinization was arrested through addition of culture media, and the cell mixtures were centrifuged at 2500 rpm for 5 minutes. Cells were counted using a hemocytometer and their viability was confirmed using trypan blue (Gibco). Cells were then seeded into 96 well tissue culture plates (VWR). MG-63, SK-OV-3, and A2780ADR cells were seeded at a density of 2,000 cells/well with a total volume of 100 µL in each well.

MDA-MB-231 cells were seeded at a density of 5,000 cells/well with a total volume of 100 µL in each well. HCT 116 and HCT 116/200 cells were seeded at a density of 4,000 cells/well with a total volume of 100 µL in each well. HUVEC cells were seeded at a density of 3,000 cells/well with a total volume of 100 µL in each well.

After seeding, the cells were incubated for 24 hours at 37° C. and 5% $CO_2$ to allow for cell attachment and renewal of the exponential growth phase. The media was then removed and replaced with media supplemented with the desired concentration of the deacetylnemorone of FIG. 1. The deacetylnemorone was stored at 4° C. until being first dissolved at 10000 µg/mL in DMSO and subsequently diluted in culture media to the desired concentration. The vehicle control was cell culture medium supplemented with 0.5% DMSO (Macron Fine Chemicals), representing the highest final concentration of DMSO used to dissolve the deacetylnemorone. For comparison, doxorubicin hydrochloride, or DOX (Sigma), and FdUrd (Sigma) supplemented treatments at concentrations sufficient to induce cell death in a majority of cells were also performed. In combination studies, the deacetylnemorone and FdUrd were first mixed into the same media and then added to the cells. At either 48 or 72 hours, the media was again removed, the cells were washed with PBS, and media containing 20% MTS solution (Promega) was added to the cells. The cells were incubated for 2 hours, and the absorbance of each well at 490 nm was measured using a Spectramax 190 microplate reader.

NCI60 Cytotoxicity Screening

One dose cytotoxicity screening was performed by the NCI-60 screening program of the National Institutes of Health (NIH), which is known in the art and available from the NIH. The NCI-60 panel is a collection of cancer cell lines, from various diverse tumors, which was developed in the 1980s by the National Cancer Institute to aid screening efforts for cytotoxic or cytostatic compounds.

In these screens 59 cell lines were utilized to determine the cytotoxic effect of the deacetylnemorone. The cell lines included: ovarian cancer cell lines OVCAR-8, IGROVI, NCI/ADR-RES, OVCAR-5, SK-OV-3, OVCAR-3, OVCAR-4; breast cancer cell lines HS578T, MDA-MB-231/ATCC, MCF7, MDA-MB-468, T-47D, BT-549; prostate cancer cell lines DU-145, PC-3; CNS cancer cell lines U251, SNB-19, SF-539, SF-268, SNB-75; SF-295; renal cancer cell lines TK-10, SN12C, CAKI-1, ACHN, UO-31, RXF 393, A498, 786-0; melanoma cell lines MDA-MB-435, UACC-257, LOX IMVI, SK-MEL-28, M14, SK-MEL-2, MALME-3M, UACC-62, SK-MEL-5; colon cancer cell lines SW-620, KM12, HT29, HCT-15, HCC-2998, COLO 205, HCT-116; non-small cell lung cancer cell lines AS49/ATCC, NCI-H23, HOP-62, NCI-H226, NCI-H322M, NCI-H460, EKVX, HOP-92, NCI-H522; and leukemia cell lines K-562, SR, CCRF-CEM, MOLT-4, HL-60(TB), RPMI-8226.

For the assay, each cell line was treated with 10 µM of deacetylnemorone to determine cytotoxicity. Each tumor cell line was maintained in RPMI 1640 media supplemented with 5% fetal bovine serum and 2 mM L-glutamine. The cells were then seeded into 96 well plates at a cell density ranging from 5,000 to 40,000 cells per well depending on the cell line (each well containing 100 µL of cell suspension). The cells were then incubated for 24 hours at 37° C., 5% $CO_2$, and 100% relative humidity to allow the cells to attach (if they were attached cell lines) and resume their growth phase. Two plates of each cell line which had not been exposed to deacetylnemorone were then fixed with TCA at the time when the deacetylnemorone was added to the remaining plates. The remaining plates were treated with 100 µL of a dilution of deacetylnemorone which had been made by diluting the compound in DMSO to 400 times the experimental concentration and subsequently diluting the solution in culture media supplemented with 50 µg/mL gentamycin to twice the experimental concentration.

A control for each cell type was also simultaneously created, which was treated with 100 µL of culture media without deacetylnemorone. The cells were then incubated for 48 hours at 37° C., 5% $CO_2$, and 100% relative humidity. In the case of the attached cell lines, the cells were then fixed in situ by the gentle addition of cold TCA (10% final TCA concentration) and incubated for 1 hour at 4° C. The plates were washed with tap water five times and air dried. The fixed cells were then incubated for 10 minutes with 100 µL of 0.4% sulforhodamine B (SRB) in 1% acetic acid. The supernatant was removed, and the plates were washed five times with 1% acetic acid and air dried. The bound stain was then dissolved in 10 mM trizma base and the absorbance was read using an automated plate reader at 515 nm.

Suspension cells were treated in the same fashion with the exception that the cells were fixed once they had settled at the bottom of the wells using 50 µL of 80% TCA. The absorbance of each well was then converted to growth percent using equation 1 (below) where $T_i$ is the average absorbance of the samples treated with a certain concentration of the compound of this invention, $T_z$ represents the average absorbance of the samples fixed at the time the compound of interest was added to the experimental groups, and C is the average absorbance of the media treated control.

$$\text{Growth Percent} = \begin{cases} \dfrac{T_i - T_z}{C - T_z} * 100, & \text{for } T_i \geq T_z \\ \dfrac{T_i - T_z}{T_z} * 100, & \text{for } T_i < T_z \end{cases} \quad (1)$$

Cell Cycle Analysis

The effect of the deacetylnemorone on the cell cycle of SKMEL5 melanoma cells was determined using a PI staining assay. SKMEL5 cells were maintained in RPMI 1640 media supplemented with 10% FBS and 2 mM L-glutamine and incubated at 37° C. and 5% $CO_2$. The cells were seeded in 6 well plates at a density of 300,000 cells per well. After 24 hours, the media was removed and replaced with either fresh media (control) or with media supplemented with 17.3 µM of the deacetylnemorone of FIG. 1. The cells were incubated with this treatment for 72 hours total. At 6, 12, 24, 48, and 72 hours, the cells from two wells each of the control of the treated group were trypsinized, collected in centrifuge tubes, and centrifuged at 2500 rpm for 5 minutes. The supernatant was removed, and the pellet was washed with PBS and centrifuged 2 times. The pellet was then suspended in 500 µL PBS and added 3 mL of 70% ethanol dropwise while vortexing. This mixture was then incubated at 4° C. for 24 hours. Next, the mixture was centrifuged, the supernatant was removed and the pellet was suspended in PBS and stored at 4° C. until all the samples were collected. Once all of the samples were prepared, the cells were again centrifuged, the supernatant was discarded, and the pellet was suspended in 500 µL of FxCycle PI/RNase staining solution and incubated at 4° C. for 24 hours before analyzing the cells using a BDLSR II flow cytometer. The cells were gated to remove cell debris and any events containing multiple cells.

In Vitro Invasion Assay

Cell migration of MDA-MB-231 breast cancer cells was assessed through making a cell-free gap with a Culture Insert 2 well 24 (Ibidi), consisting of two wells that were separated by a wall. A total of 70 µl of cell suspension comprising of 35×10³ cells was added to each well. Cells were given 24 hours to attach and reach confluency. Culture inserts were then removed and cell debris was washed with PBS. Fresh culture media supplemented with different concentration of the compound of interest was added to the wells and the cells were incubated at 37° C. and 5% $CO_2$ for 26 hours. Images were taken 0, 6, 20, and 26 hours after compound addition using a phase contrast Nikon Eclipse Ti-E inverted microscope. Quantification of invasion was performed by measuring the gap distance for three repetitions and using the following formula, $$\text{Invasion \%} = \frac{(W_0 - W_n)}{W_0} * 100\% \quad (2)$$

where $W_n$ is the width of gap after incubation, and $W_0$ is the initial width right after forming the gap.

Tube Formation Assay

Growth factor reduced BD Matrigel (Corning), stored long-term at −20° C., was thawed on ice overnight in a 4° C. refrigerator prior to use. The following day, 50 µL of the thawed Matrigel was added to each well of a pre-chilled 96-well plate and incubated at 37° C. and 5% $CO_2$ for approximately 30 minutes to allow the matrix to form a gel. Next, 100 µL of a cell suspension containing 20,000 HUVEC cells in cell culture media with various concentrations of deacetylnemorone was added to each well. The control consisted of HUVEC cells suspended in endothelial growth media alone. After 8 hours of incubation at 37° C. and 5% CO2, the number of tubes formed between the endothelial cells were quantified using an inverted microscope (Invitrogen EVOS FL Auto at 4× magnification).

Results

Figure 9:
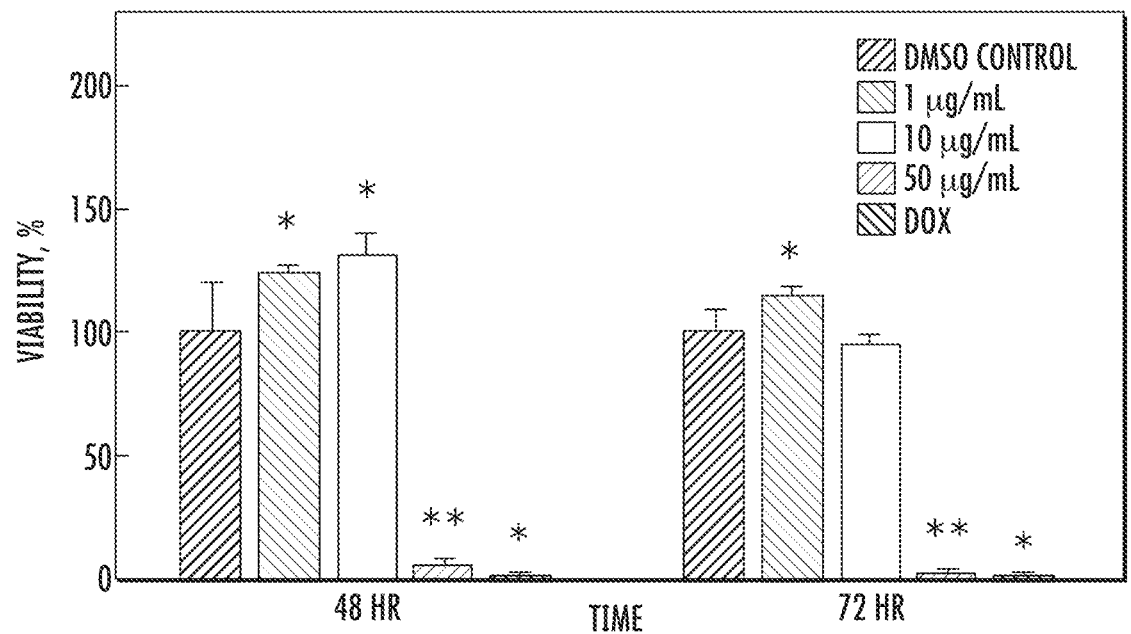
FIG. 9 presents the percent viability of MG-63 cancer cells in response to various concentrations of a deacetylnemorone after 48 and 72 hours of exposure.
Figure 10:
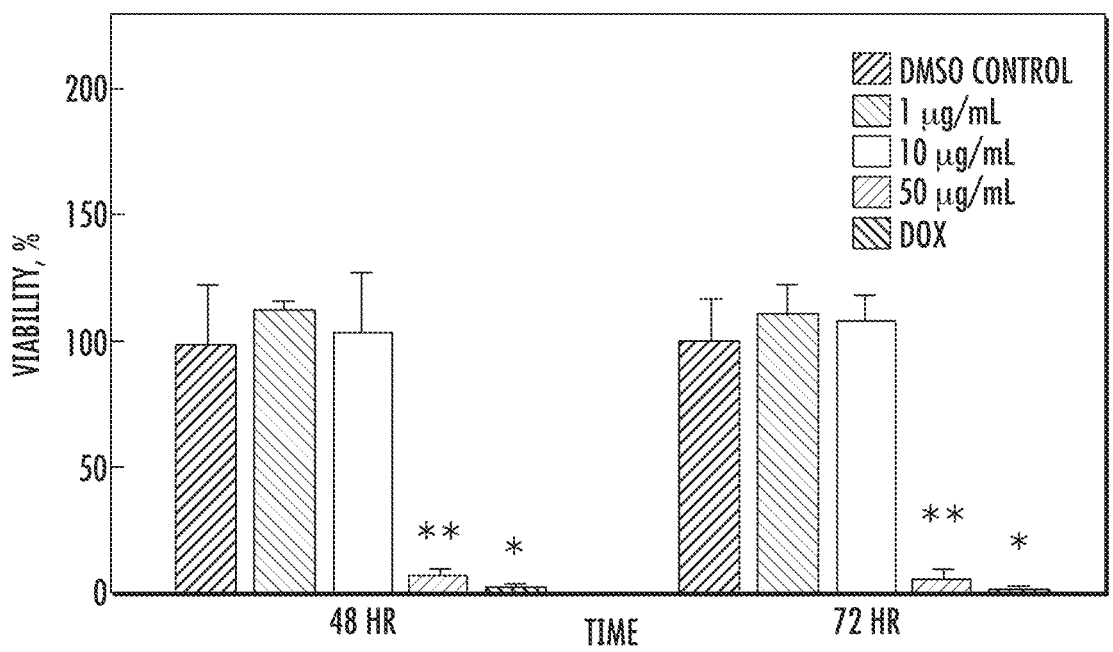
FIG. 10 presents the percent viability of SK-OV-3 cancer cells in response to various concentrations of a deacetylnemorone after 48 and 72 hours of exposure.
Figure 11:
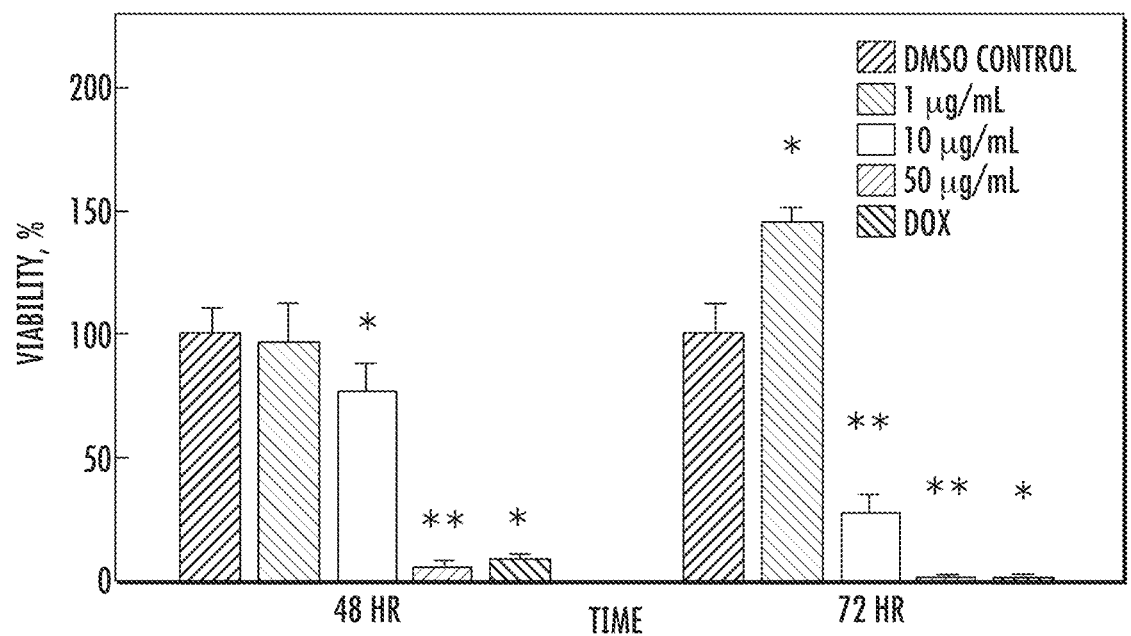
FIG. 11 presents the percent viability of MDA-MB-231 cancer cells in response to various concentrations of a deacetylnemorone after 48 and 72 hours of exposure.
Figure 12:
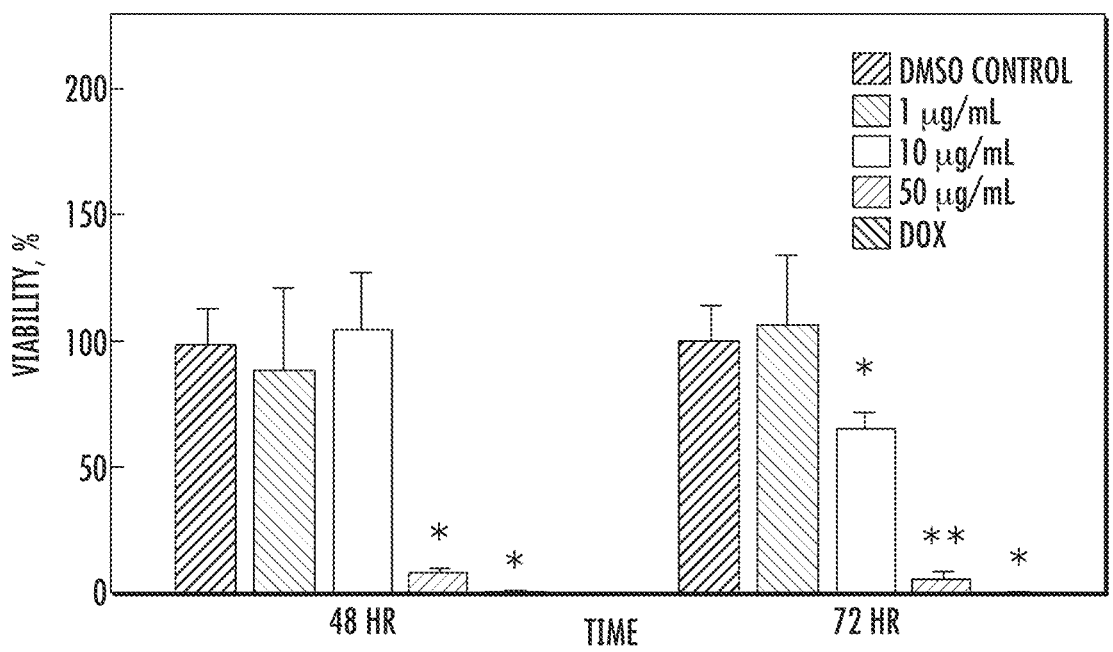
FIG. 12 presents the percent viability of HCT-116 cancer cells in response to various concentrations of a deacetylnemorone after 48 and 72 hours of exposure.
Figure 13:
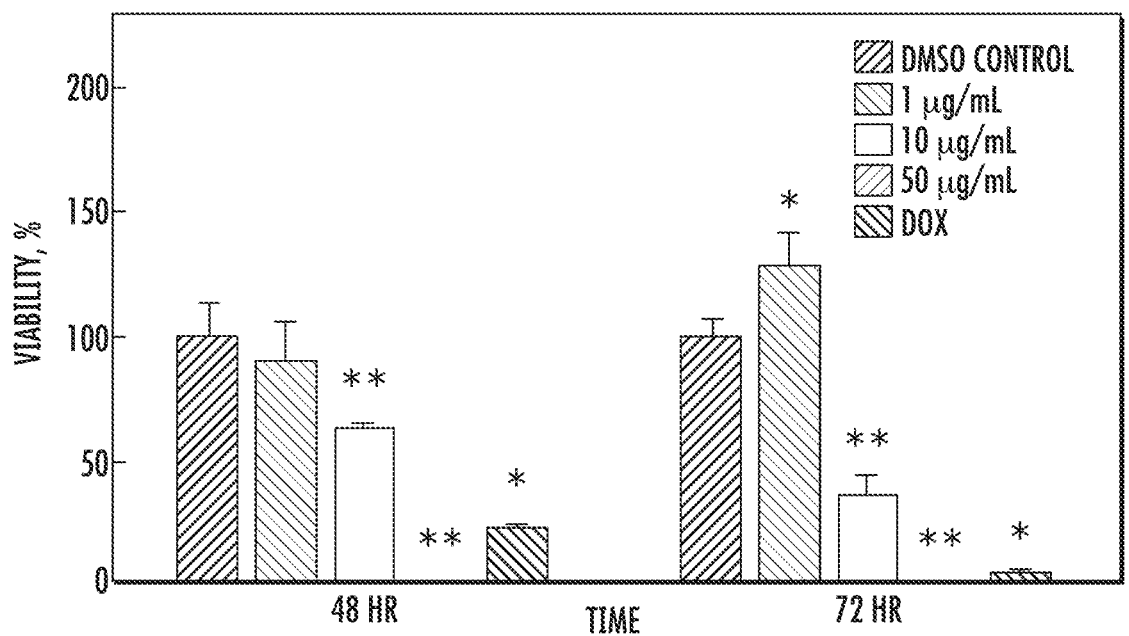
FIG. 13 presents the percent viability of HCT 116/200 cancer cells in response to various concentrations of a deacetylnemorone after 48 and 72 hours of exposure.
Figure 14:
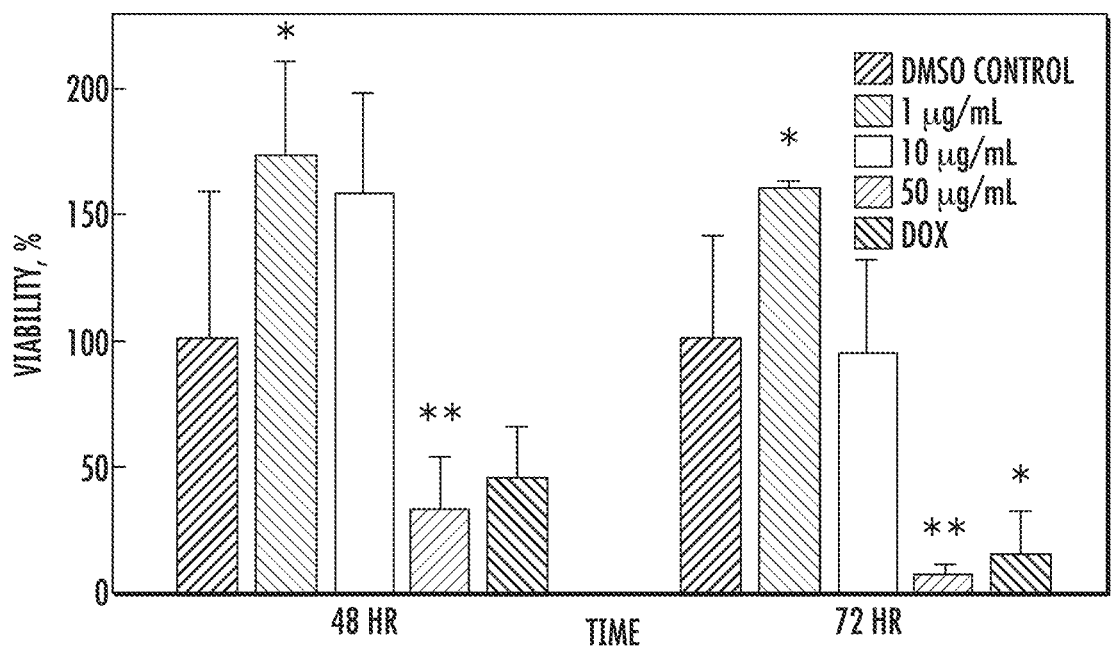
FIG. 14 presents the percent viability of A2789ADR cancer cells in response to various concentrations of a deacetylnemorone after 48 and 72 hours of exposure.

The deacetylnemorone showed significant cytotoxic properties against all cell lines screened with MTS assay at all time points as shown in FIG. 9 (MG-63 cancer cells), FIG. 10 (SK-OV-3 cancer cells), FIG. 11 (MDA-MB-231 cancer cells), FIG. 12 (HCT-116 cancer cells), FIG. 13 (HCT 116/200 cancer cells) and FIG. 14 (A2789ADR cancer cells). The effective dose varied from cell line to cell line, but cell death was indicated using the MTS assay at concentrations as low as 10 µg/mL in breast and colon cancer.

Figure 15:
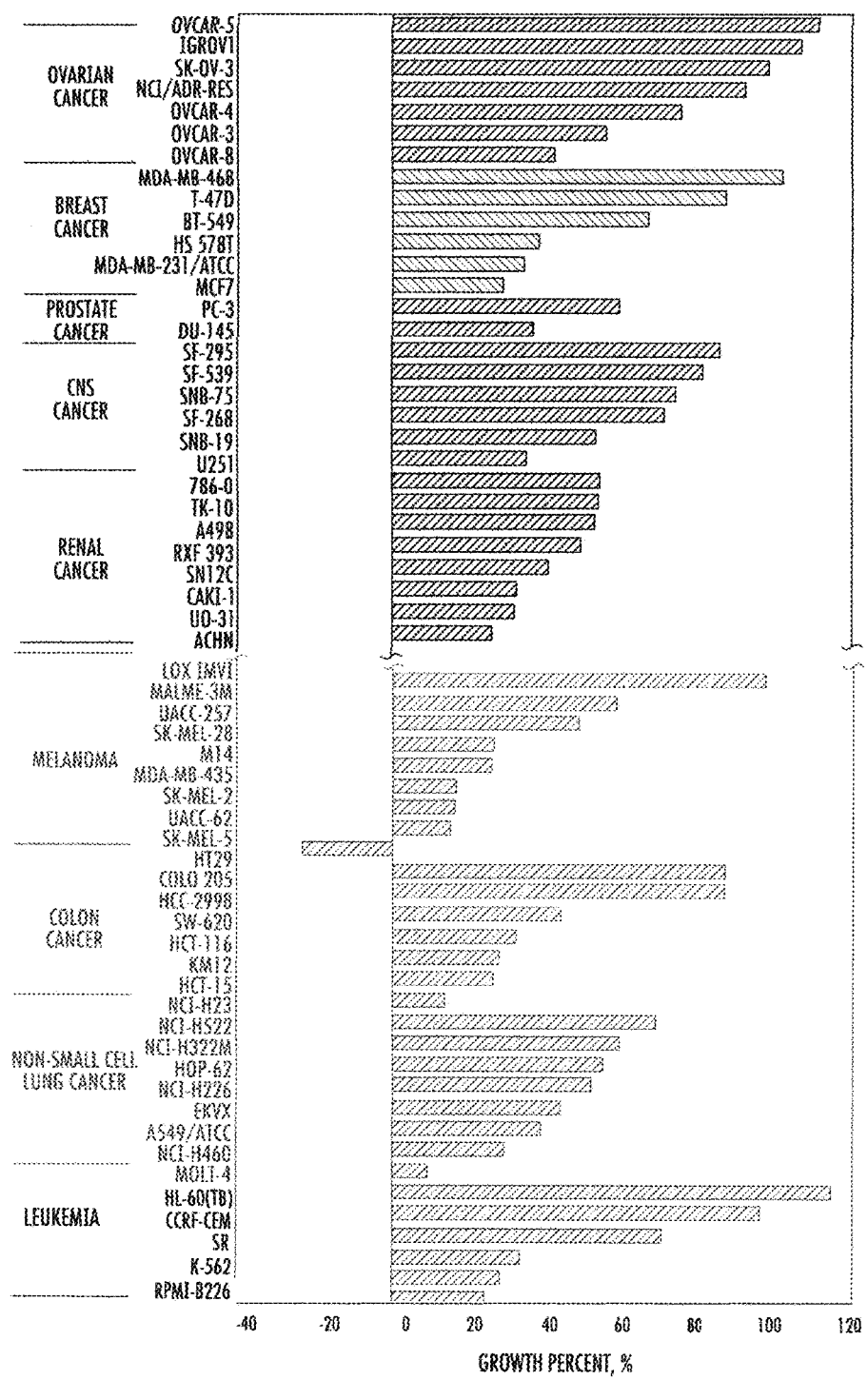
FIG. 15 presents a waterfall plot of the growth percent of 59 cell lines in response to 10 µM of a deacetylnemorone as determined by a NCI-60 one-dose screen.

The anti-proliferative effect of deacetylnemorone was confirmed by the NCI-60 screen as seen in FIG. 15. The growth of 55 of the 59 cell lines screened was inhibited by the deacetylnemorone, and the average percent growth across all 59 cell lines had been inhibited by 47% after 48 hours. The deacetylnemorone appeared to be particularly effective against melanoma, inhibiting the growth of 6 out of 9 melanoma cell lines by more than 70%. Additionally, a negative percent growth was observed in the melanoma line SK-MEL-5. This negative percent growth of this melanoma line confirms that deacetylnemorone is able to induce cell death in certain cell lines while sparing others.

Figure 16:
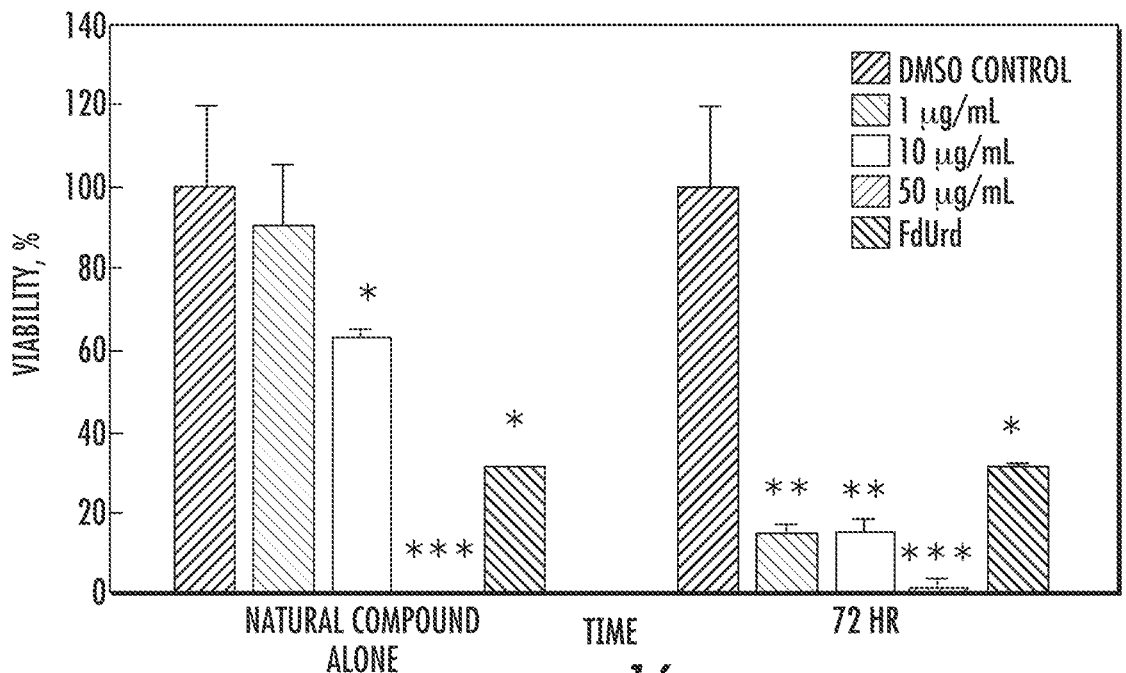
FIG. 16 presents the percent viability of HCT 116/200 cancer cells in response to a 48 hour exposure of a deacetylnemorone alone and in conjunction with 5-fluoro-2'-deoxyuridine (FdUrd).
Figure 17:
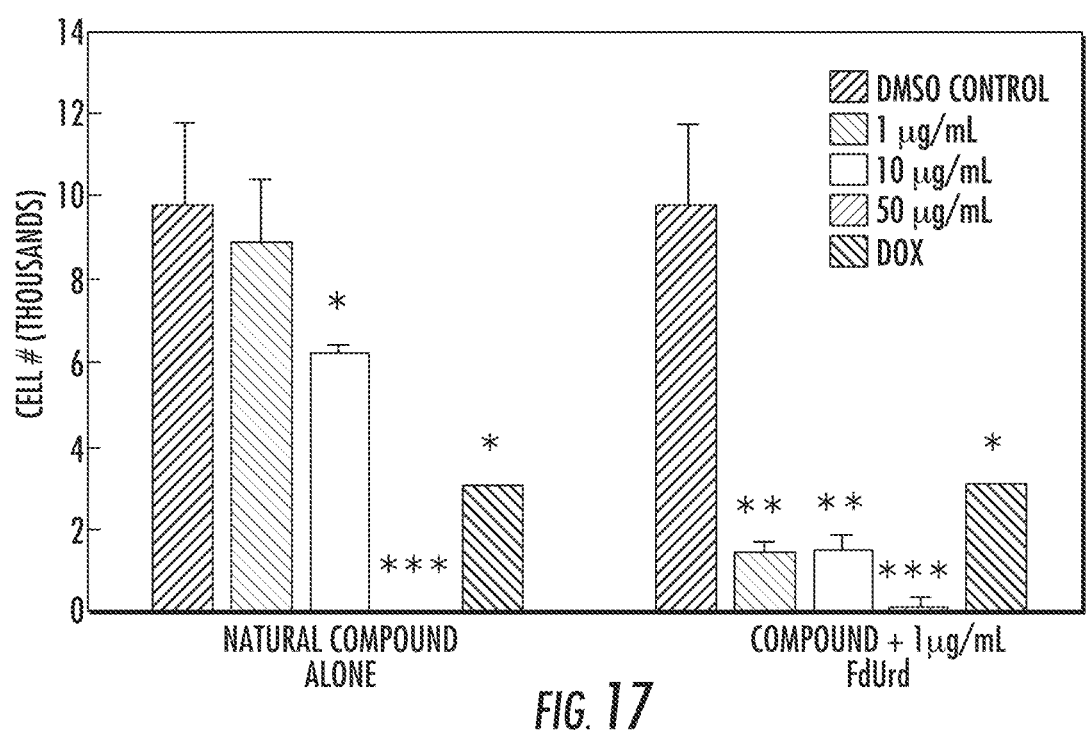
FIG. 17 presents the cell number of HCT 116/200 cancer cells in response to a 48 hour exposure of a deacetylnemorone alone and in conjunction with 5-fluoro-2'-deoxyuridine (FdUrd).

A dose dependent, synergistic cytotoxic effect was observed when the deacetylnemorone was used in combination with FdUrd as seen in FIG. 16 and FIG. 17. This synergistic effect was observed using lower concentrations of deacetylnemorone than was capable of eliciting a cytotoxic response alone. This speaks to the ability of deacetylnemorone to induce desired levels of cell death when in combination with other chemotherapy agents while simultaneously limiting the dosage of both the accepted chemotherapy agent and the deacetylnemorone itself.

Figure 19A:
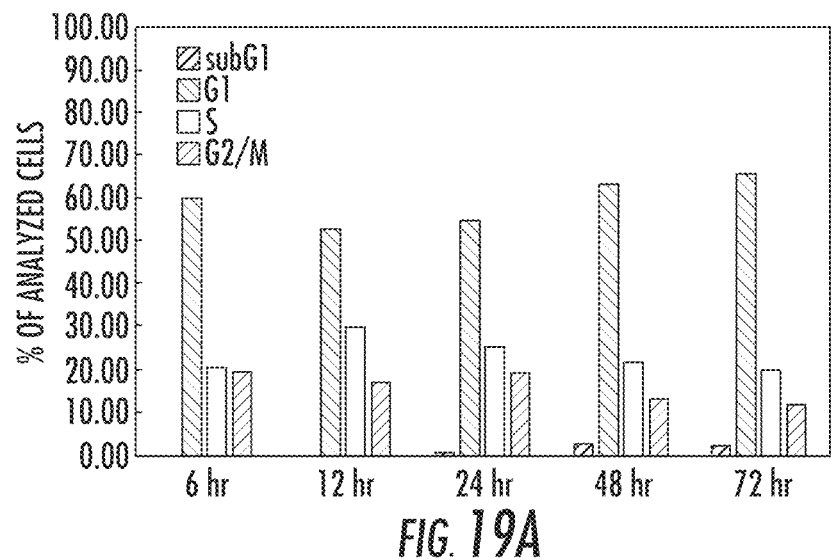
FIG. 19A presents cell cycle flow cytometry data showing the percent of analyzed SKMEL5 cells in each phase of the cell cycle after four different time points of treatment with control.
Figure 19B:
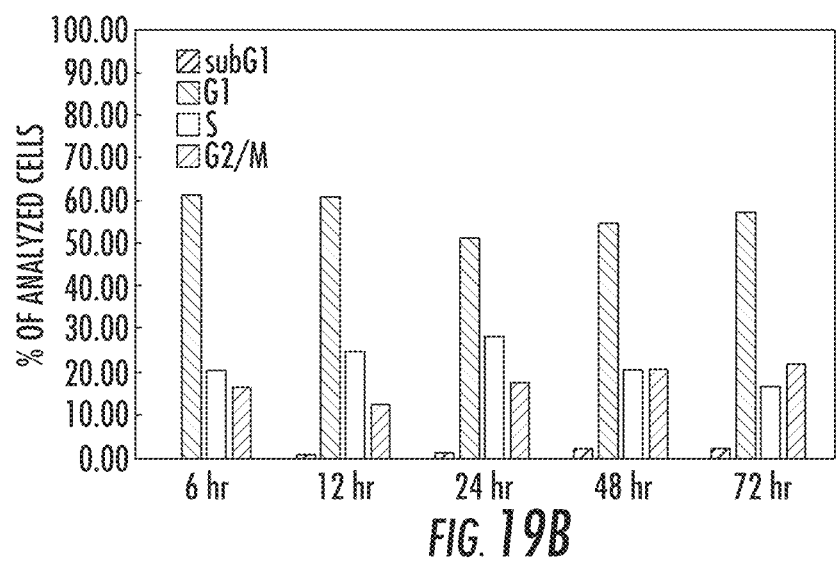
FIG. 19B presents cell cycle flow cytometry data showing the percent of analyzed SKMEL5 cells in each phase of the cell cycle after four different time points of treatment with 15 µM of a diacetylnemorone.

In addition to causing cell death in a number of cancer cell types, the deacetylnemorone demonstrated an ability to disrupt the cell cycle as shown in FIG. 18, FIG. 19A, and FIG. 19B. SKMEL5 melanoma cells incubated with the compound exhibited an increase in the percent of cells in S phase after 24 hours. An increase in S phase is associated with inhibition of DNA or protein synthesis before mitosis can occur. As time progressed, the cells which had been slowed through S phase gradually entered G2/M by the 72 hour time point. A low sub-G1 population over the same time scale suggests that the cells are either not dying or dying through a non-apoptotic pathway. These results suggest that the deacetylnemorone is interfering with cell growth and division which will potentiate a cytostatic effect on rapidly growing cancerous cells. Further, higher concentration of deacetylnemorone has the potential to fully arrest cell cycle progression and lead to cell death.

Figure 20:
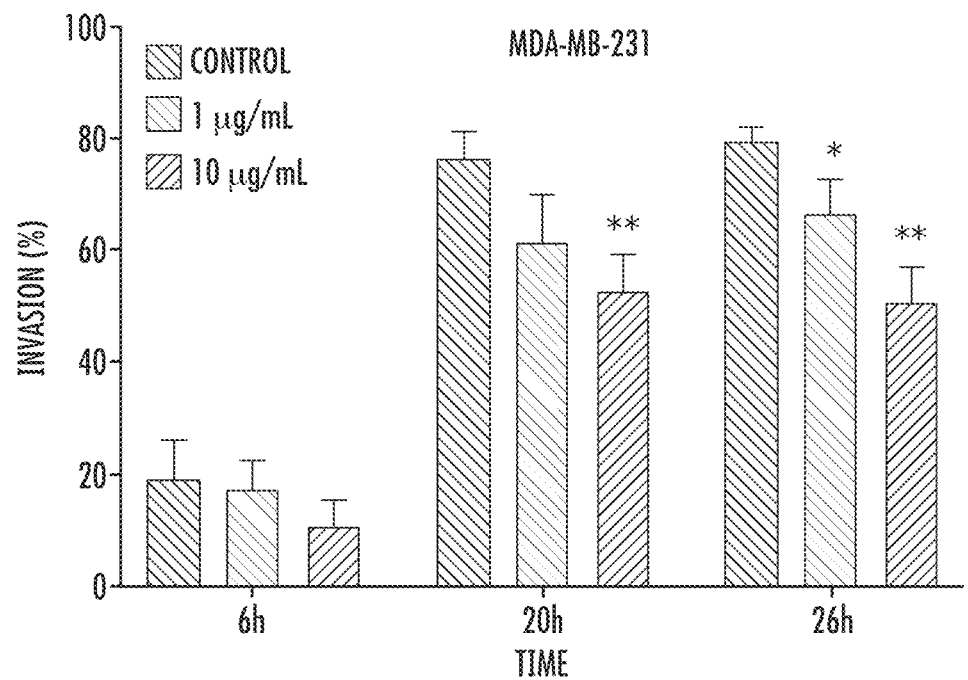
FIG. 20 presents the results of an invasion assay of MDA-MB-231 breast cancer cells when incubated with 1 or 10 µg/mL of a deacetylnemorone 6, 20, and 26 hours. (Significant difference from the control of the same time point was denoted by * $p \le 0.05$, ** $p \le 0.01$).
Figure 21:
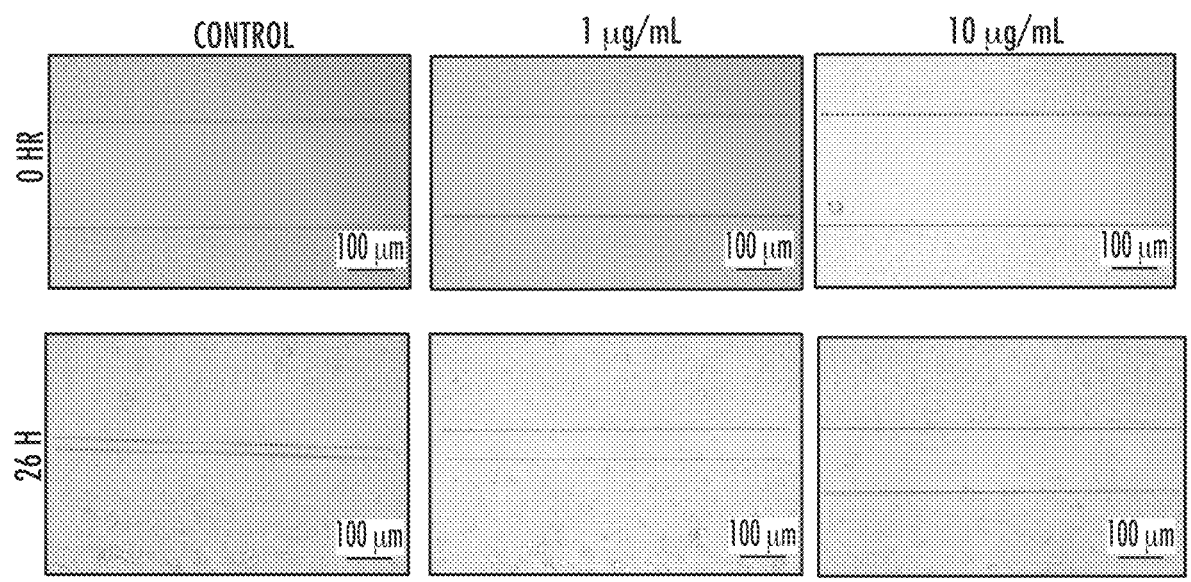
FIG. 21 presents representative images of the cells of FIG. 20 at 0 and 26 hours after insert removal and compound addition.
Figure 22:
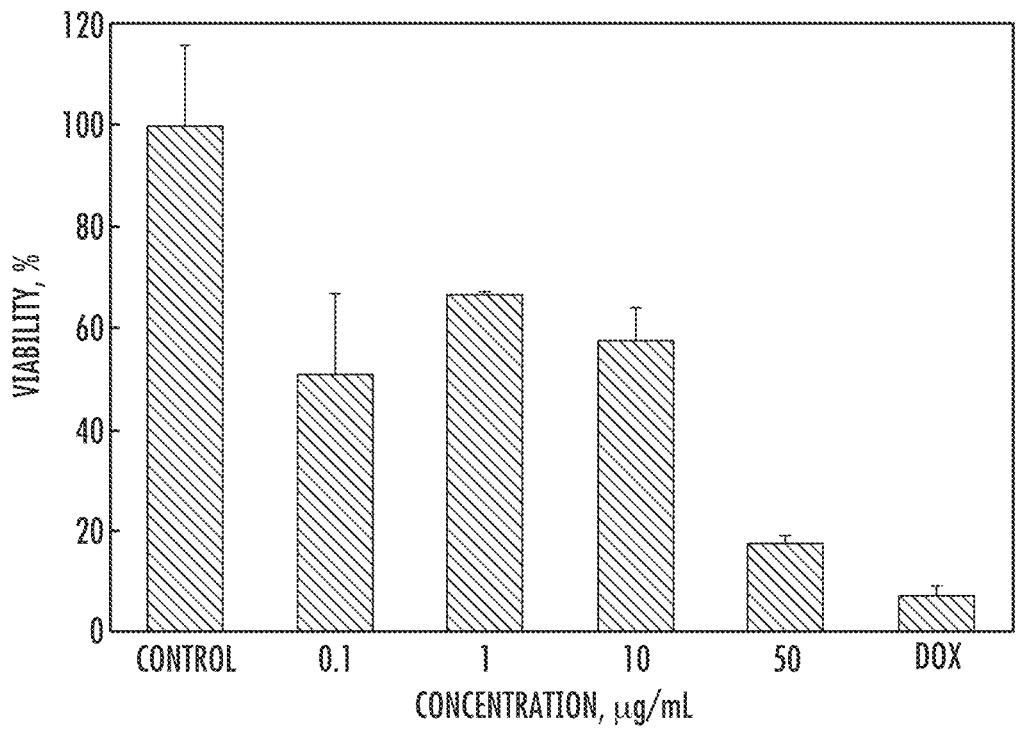
FIG. 22 presents the percent viability of HUVEC endothelial cells in response to 48 hours of incubation with various concentrations of a deacetylnemorone. The DOX control was incubated with 1 µg/mL DOX.
Figure 23:
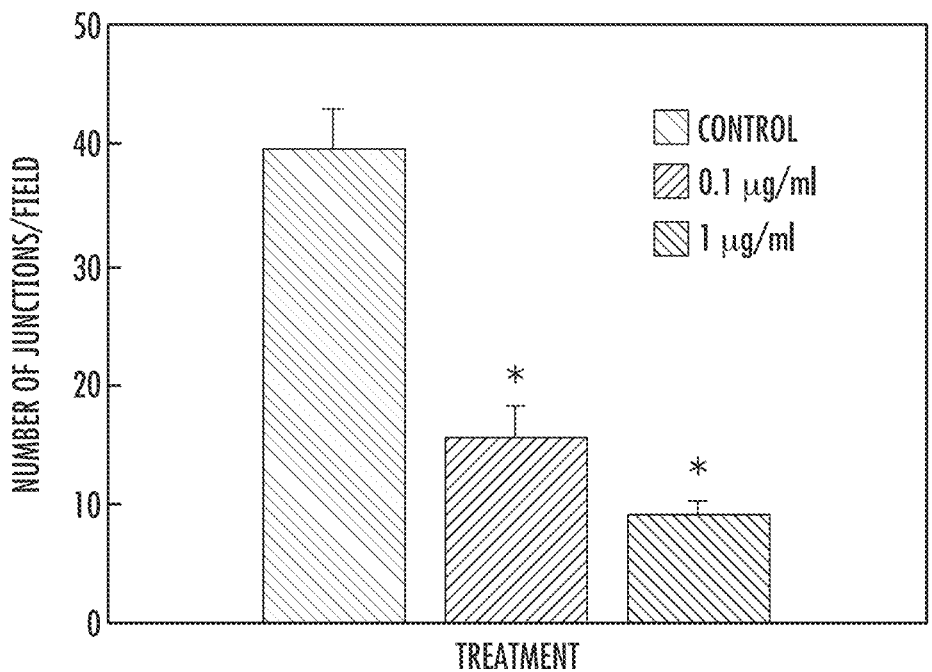
FIG. 23 presents the average number of junctions, or tubes, formed between HUVEC endothelial cells after 8 hours of incubation on growth factor reduced BD Matrigel with growth media alone and with various concentrations of a deacetylnemorone.
Figure 24A:
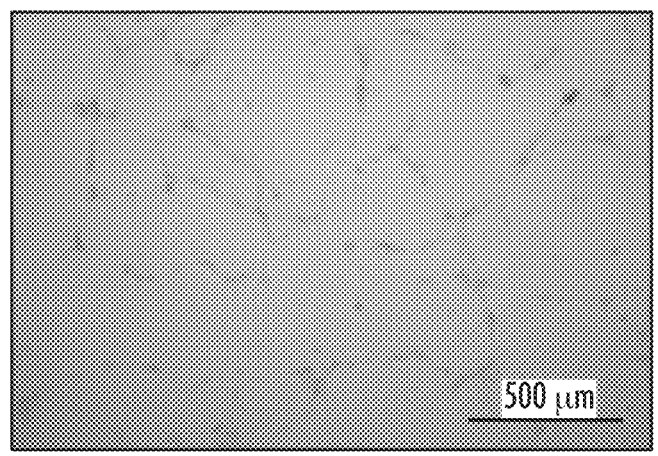
FIG. 24A is a representative bright field image of the incubation of HUVEC endothelial cells on growth factor reduced BD Matrigel in growth media alone.
Figure 24B:
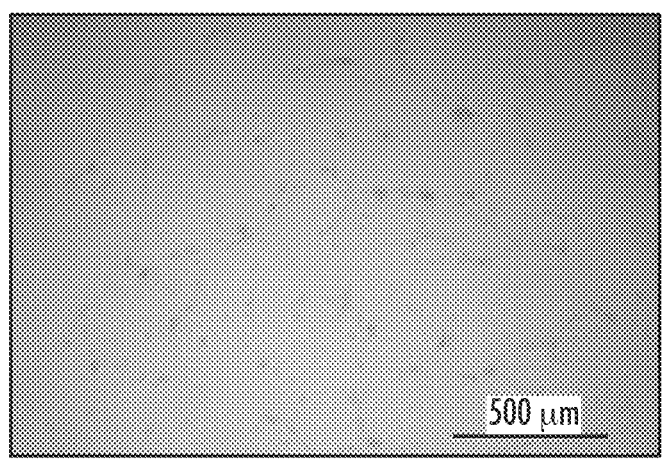
FIG. 24B is a representative bright field image of the incubation of HUVEC endothelial cells on growth factor reduced BD Matrigel in growth media including 0.1 µg/mL deacetylnemorone.
Figure 24C:
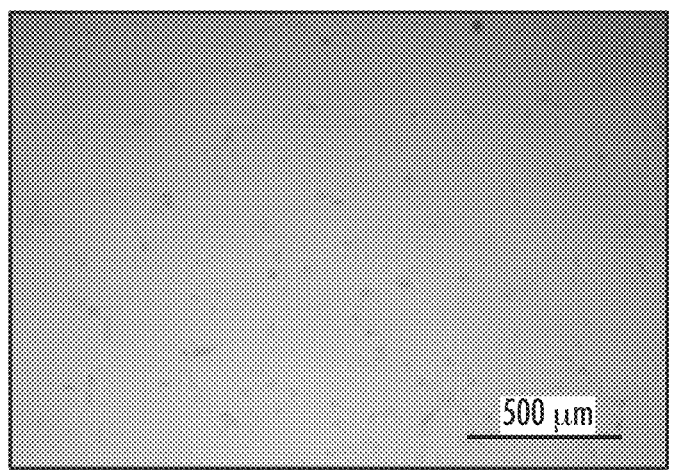
FIG. 24C is a representative bright field image of the incubation of HUVEC endothelial cells on growth factor reduced BD Matrigel in growth media including 1 µg/mL deacetylnemorone.

Deacetylnemorone has further shown an ability to inhibit the invasion of breast cancer cells in vitro. As shown in FIG. 20 and FIG. 21, the invasive ability of breast cancer cells was significantly inhibited by 1 or 10 µg/mL of deacetylnemorone after 26 hours. Invasion was also significantly inhibited after 20 hours of incubation after just 20 hours.

Deacetylnemorone was additionally able to inhibit tube formation between HUVEC cells at 0.1 and 10 µg/mL concentrations as shown in FIG. 22, FIG. 23, and FIG. 24A-24C. The tube formation assay is used to model the formation of new blood vessels, and as a result, this finding demonstrates the potential of deacetylnemorone to act as an antiangiogenic agent. By inducing a cytotoxic effect on cancer cells, diminishing the invasive property of the cells, and inhibiting angiogenesis, deacetylnemorone may be able to attack tumor growth, tumor formation, and metastasis through a multipronged mechanism.

While certain embodiments of the disclosed subject matter have been described using specific terms, such description is for illustrative purposes only, and it is to be understood that changes and variations may be made without departing from the spirit or scope of the subject matter.

What is claimed is:

1. A method for inhibiting growth and development of cancer cells, the method comprising delivering a deacetylnemorone abietane diterpenoid to an area comprising cancer cells, the cancer cells comprising breast cancer cells, ovarian cancer cells, melanoma cells, colon cancer cells, or osteosarcoma cells, the deacetylnemorone abietane diterpenoid having a structure of:

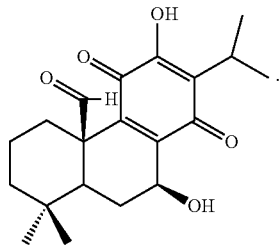

2. The method of claim 1, wherein the deacetylnemorone is delivered to the cancer cells such that the deacetylnemorone contacts the cancer cells at a concentration of about 10 millimolar or greater.

3. The method of claim 1, wherein the deacetylnemorone is delivered to the cancer cells such that the deacetylnemorone contacts the cancer cells at a concentration of from about 10 millimolar to about 50 millimolar.

4. The method of claim 1, wherein the deacetylnemorone is delivered to the area in multiple doses.

5. The method of claim 1, the method comprising delivering the deacetylnemorone to the cancer cells in conjunction with a second bioactive agent.

6. The method of claim 5, the method comprising delivering the deacetylnemorone and the second bioactive agent to the cancer cells together in a single composition.

7. The method of claim 5, the method comprising delivering the deacetylnemorone separately from the delivery of the second bioactive agent to the area.

8. The method of claim 5, wherein the second bioactive agent comprises a chemotherapy agent.

9. The method of claim 8, wherein the chemotherapy agent comprises 5-fluoro-2'-deoxyuridine.

10. The method of claim 1, wherein the cancer cells are resistant to one or more chemotherapy agents.

11. The method of claim 1, wherein the cancer cells comprise breast cancer cells.

12. The method of claim 1, wherein the cancer cells comprise ovarian cancer cells.

13. The method of claim 1, wherein the cancer cells comprise melanoma cells.

14. The method of claim 1, wherein the cancer cells comprise colon cancer cells.

* * * * *